(12) United States Patent
Carruthers et al.

(10) Patent No.: US 6,951,882 B2
(45) Date of Patent: Oct. 4, 2005

(54) SUBSTITUTED 4-PHENYL-[1,3]-DIOXANES

(75) Inventors: Nicholas I Carruthers, Poway, CA (US); Todd K. Jones, Solana Beach, CA (US); Xiaobing Li, Flemington, NJ (US); Timothy W. Lovenberg, San Diego, CA (US); Laura C. McAtee, King of Prussia, PA (US); Victor K. Phuong, San Diego, CA (US); Dale A. Rudolph, San Diego, CA (US); Steven W. Sutton, Carlsbad, CA (US)

(73) Assignee: Janssen Pharmaceutica N.V. (BE)

( * ) Notice: Subject to any disclaimer, the term of this patent is extended or adjusted under 35 U.S.C. 154(b) by 0 days.

(21) Appl. No.: 10/734,800

(22) Filed: Dec. 12, 2003

(65) Prior Publication Data

US 2004/0147593 A1 Jul. 29, 2004

Related U.S. Application Data

(60) Provisional application No. 60/433,192, filed on Dec. 12, 2002.

(51) Int. Cl.$^7$ ..................... A61K 31/357; C07D 319/06
(52) U.S. Cl. ...................... 514/452; 514/314; 514/444; 546/173; 549/59; 549/371
(58) Field of Search .................. 549/59, 371; 514/444, 514/452, 314; 546/173

(56) References Cited

PUBLICATIONS

PCT International Search Report, dated May 12, 2004, for PCT Int'l. Appln. No. PCT/US03/40136.
Alo, B.I. et al. Sequential Directed Ortho Metalation–Boronic Acid Cross Coupling Reactions. A General Regiospecific Route to Oxygenated Dibenzo[b,d]pyran–6–ones Related to Ellagic Acid. J. Org. Chem. 1991, 56:3763–3768.
Ammoun, S. et al. Distinct Recognition of OX1 and OX2 Receptors by Orexin Peptides. J. Pharmacol. Exp. Ther. 2003, 305(2):507–514.
Blanco, M. et al. Cellular Localization of Orexin Receptors in Human Pituitary. J. Clin. Endocrinol. Metab. 2001, 86(4):1616–1619.
Chemelli, R.M. et al. Narcolepsy in Orexin Knockout Mice: Molecular Genetics and Sleep Regulation. Cell 1999, 98(4):437–451.
Chen, C.–T.et al. Pressor Effects of Orexins Injected Intracisternally and to Rostral Ventrolateral Medulla of Anesthetized Rats. Am. J. Physiol. 2000, 278(3):R692–R697.
Drouot, X. et al. Low Levels of Ventricular CSF Orexin/Hypocretin in Advanced PD. Neurology 2003, 61(4):540–543.
Fults, D. et al. Establishment and Characterization of a Human Primitive Neuroectodermal Tumor Cell Line from the Cerebral Hemisphere. J. Neuropathol. Exp. Neurol. 1992, 51(3):272–280.

Hara, J. Genetic Ablation of Orexin Neurons in Mice Results in Narcolepsy, Hypophagia, and Obesity. Neuron 2001, 30(2):345–354.
Kirchgessner, A.L. and M.–T. Liu. Orexin Synthesis and Response in the Gut. Neuron 1999, 24(4):941–951.
Larsson, K.P. et al. The STC–1 Cells Express Functional Orexin–A Receptors Coupled to CCK Release. Biochem. Biophys. Res. Commun. 2003, 309(1):209–216.
Lin, L. et al. The Sleep Disorder Canine Narcolepsy Is Caused by a Mutation in the Hypocretin (Orexin) 2 Receptor Gene. Cell 1999, 98(3):365–376.
Lubkin, M. and A. Stricker–Krongrad. Independent Feeding and Metabolic Actions of Orexins in Mice. Biochem. Biophys. Res. Commun. 1998, 253(2):241–245.
Mignot, E. et al. Complex HLA–DR and –DQ Interactions Confer Risk of Narcolepsy–Cataplexy in Three Ethnic Groups. Am. J. Hum. Genet. 2001, 68(3):686–699.
Mignot, E. and E. Thorsby, Narcolepsy and the HLA System. N. Engl. J. Med. 2001, 344(9):692.
Miyaura, N. and A. Suzuki. Palladium–Catalyzed Cross–Coupling Reactions of Organoboron Compounds: Chem. Rev. 1995, 95:2457–2483.
Nakamura, T. et al. Orexin–Induced Hyperlocomotion and Stereotypy Are Mediated by the Dopaminergic System. Brain Res. 2000, 873(1):181–187.
Nordin, I.C. and J.A. Thomas. An Improved Synthesis of (4S,5S)–2,2–Dimethyl–4–phenyl–1,3–dioxan–4–amine. Tetrahedron Lett. 1984, 25(50):5723–5724.
Peyron, C. et al. Neurons Containing Hypocretin (Orexin) Project to Multiple Neuronal Systems. J. Neurosci. 1998, 18(23):9996–10015.
Peyron, C. et al. A Mutation in a Case of Early Onset Narcolepsy and a Generalized Absence of Hypocretin Peptides in Human Narcoleptic Brains. Nat. Med. 2000, 6(9):991–997.
Piper, D.C. et al. The Novel Brain Neuropeptide, Orexin–A, Modulates the Sleep–Wake Cycle of Rats. Eur. J. Neurosci. 2000, 12(2):726–730.
Sakurai, T. et al. Orexin and Orexin Receptors: A Family of Hypothalamic and G Protein–Coupled Receptors that Regulate Feeding Behavior. Cell 1998, 92(4):573–585.
Samson, W.K. et al. Cardiovascular Regulatory Actions of the Hypocretins in Brain. Brain Res. 1999, 831(1–2):248–253.
Shirasaka, T. et al. Sympathetic and Cardiovascular Actions of Orexins in Conscious Rats. Am. J. Physiol. 1999, 277(6, Pt.2):R1780–R1785.

(Continued)

*Primary Examiner*—Bernard Dentz

(57) ABSTRACT

Urea-containing, substituted 4-phenyl-[1,3]-dioxanes, methods of manufacturing them, compositions containing them, and methods of using them to treat, for example, obesity or a sleep/wake disorder mediated by orexin-2 are described.

44 Claims, No Drawings

OTHER PUBLICATIONS

Takahashi, N. et al. Stimulation of Gastric Acid Secretion of Centrally Administered Orexin–A in Conscious Rats. Biochem. Biophys. Res. Commun. 1999, 254(3):623–627.

Van Den Pol, A.N. Hypothalamic Hypocretin (Orexin): Robust Innervation of the Spinal Cord. J. Neurosci. 1999, 19(8):3171–3182.

Willie, J.T. et al. Distinct Narcolepsy Syndromes in Orexin Receptor–2 and Orexin Null Mice: Molecular Genetic Dissection of Non–REM and REM Sleep Regulatory Processes. Neuron 2003, 38(5):715–730.

Yamanaka, A. et al. Orexins Activate Histaminergic Neurons via the Orexin 2 Receptor. Biochem. Biophys. Res. Commun. 2002, 290(4):1237–1245.

Morie, Toshiya et al., "Convenient Synthesis of N–(2, 2–Dimethyl–1,3–Dioxan–5–YL)1H–Indazol E–3–Carboxamide", Synthetic Communications, vol. 27, No. 4, pp. 559–566, 1997.

Comgenex Product List, Database Chemcats 'Online!, Chemical Abstracts Service, Order Nos. CGX–0377921, CGX–0377920, CGX–0145248Columbus, Ohio.

SUBSTITUTED 4-PHENYL-[1,3]-DIOXANES

This application claims priority from Provisional Application 60/433192 filed Dec. 12, 2002.

FIELD OF THE INVENTION

This invention relates to a series of urea-containing substituted 4-phenyl-[1,3]-dioxanes, pharmaceutical compositions containing these compounds, and intermediates used in their manufacture, and methods of using them.

BACKGROUND OF THE INVENTION

In the central nervous system neurons expressing preproorexin, the precursor from which orexin is produced, are found in the perifornical nucleus, the dorsal hypothalamus and the lateral hypothalamus (C. Peyron et al., *J. Neurosci.*, 1998, 18(23): 9996–10015). Orexinergic cells in these nuclei project to many areas of the brain, extending rostrally to the olfactory bulbs and caudally to the spinal chord (A. N. van den Pol, *J. Neurosci.*, 1999, 19(8): 3171–3182). The orexins bind to two high affinity receptors, termed Orexin-1 and Orexin-2 receptors. The orexin-1 receptor is selective in favor of orexin A, while the orexin-2 receptor binds both orexins with similar affinities. The broad CNS distribution of orexin projections and neurons expressing orexin receptors is suggestive of orexin involvement in a number of physiological functions such as feeding, drinking, arousal, stress, metabolism and reproduction. A recent paper describing targeted necrosis of cells expressing prepro-orexin suggests the most physiologically important roles of the orexins are likely to be effects on arousal, feeding and metabolism (J. Hara et al., *Neuron*, 2001, 30:345–354). A prominent orexin neuronal projection via the vagus nerve probably mediates published central orexin effects on cardiac parameters (W. K. Samson et al., *Brain Res.*, 1999, 831:248–253; T. Shirasaka et al., *Am. J. Physiol.*, 1999, 277:R1780–R1785; C.-T. Chen et al., *Am. J. Physiol.*, 2000, 278:R692–R697), gastric acid secretion and gastric motility (A. L. Kirchgessner and M.-T. Liu, *Neuron*, 1999, 24:941–951; N. Takahashi et al., *Biochem. Biophys. Res. Commun.*, 1999, 254:623–627).

A number of factors suggest the orexin system is an important modulator of arousal. Orexin given i.c.v. increases the time rodents spend awake (D. C. Piper et al., *Eur. J. Neurosci.*, 2000, 12:726–730) as measured using EEG and EMG recordings. Orexin-mediated effects on arousal are linked to orexin neuronal projections to histaminergic neurons in the tuberomammillary nucleus and can be blocked with an H1 antihistamine (A. Yamanaka et al., *Biochem. Biophys. Res. Commun.*, 2002, 290:1237–1245). TMN histaminergic neurons express orexin-2 receptor and less orexin-1 receptor. Rodents whose pre-pro orexin gene has been knocked out (R. M. Chemelli et al., *Cell*, 1999, 98:437–451) or whose orexigenic neurons have been killed (J. Hara et al.) display altered sleep/wake cycles similar to narcolepsy. The dog models of narcolepsy have been shown to have a mutant and non-functional orexin-2 receptor (L. Lin et al., *Cell*, 1999, 98:365–376). Human narcolepsy appears to be linked to deficient orexin signaling, most likely related to immune ablation of orexinergic neurons in the lateral hypothalamus (E. Mignot et al., *Am. J. Hum. Genet.*, 2001, 68:686–699; E. Mignot and E. Thorsby, *N. Engl. J. Med.*, 2001, 344(9):692). In rare cases human narcoleptics have also been identified with mutant orexin-2 receptors (C. Peyron et al., *Nat. Med.*, 2000, 6(9):991–997).

Disorders of the sleep-wake cycle are therefore likely targets for orexin-2 receptor antagonist therapy. Examples of such disorders include sleep-wake transition disorders, insomnia, restless legs syndrome, jet-lag and sleep disorders secondary to neurological disorders (manias, depressions, manic depression, schizophrenia, pain syndromes and the like).

The orexin system also interacts with brain dopamine systems. Intracerebroventricular injections of orexin increase locomotor activity, grooming and stereotypy; these behavioral effects are reversed by administration of D2 dopamine receptor antagonists (T. Nakamura et al., *Brain Res.*, 2000, 873:181–187). Orexin-2 antagonists may therefore be useful to treat neurological disorders such as Parkinson's Disease, Gilles de la Tourette's Syndrome, anxiety, delirium and dementias.

Effects of the orexins on body weight are likely to be mediated by orexin-mediated increases in appetite (T. Sakurai et al., *Cell*, 1998, 92:573–585) and alterations in metabolism (M. Lubkin and A. Stricker-Krongrad, *Biochem. Biophys. Res. Commun.*, 1998, 253:241–245). Some orexin effects on appetite and metabolism may be mediated in the gut, where orexins alter gastric acid secretion and gastric motility. Orexin antagonists are therefore likely therapies for obesity and may, through weight loss, be useful to treat consequences of obesity such as insulin resistance/type 2 diabetes, hyperlipidemia, gallstones, angina, high blood pressure, breathlessness, infertility, sleep apnea, back pain, joint pain, varicose veins and osteoarthritis. Conversely, the orexin system appears to be involved in anorectic/bulemic/ exercise related amenorrhea and could therefore be useful in fertility control.

Orexins and their receptors have been found in both the myenteric and submucosal plexus of the enteric nervous system (A. L. Kirchgessner and M.-T. Liu). The orexins have been shown to increase motility in vitro (A. L. Kirchgessner and M.-T. Liu) and to stimulate gastric acid secretion in vivo (N. Takahashi et al.). Orexin effects on the gut may be driven by a projection via the vagus nerve (A. N. van den Pol), as vagotomy or atropine prevent the effect of a central (i.c.v) injection of orexin on gastric acid secretion (N. Takahashi et al.). Orexin antagonists are therefore potential treatments for ulcers, irritable bowel syndrome, diarrhea and gastroesophageal reflux.

Intracerebroventricularly administered orexins have been shown to increase mean arterial pressure and heart rate in freely moving (awake) animals (W. K. Samson et al.; T. Shirasaka et al.) and in urethane anaesthetized animals (C.-T. Chen et al.), with similar results. Orexin antagonists are therefore candidates for treatment of hypertension, angina pectoris, arrhythmias and acute heart failure.

SUMMARY OF THE INVENTION

The present invention concerns compounds that can be represented by formula (I):

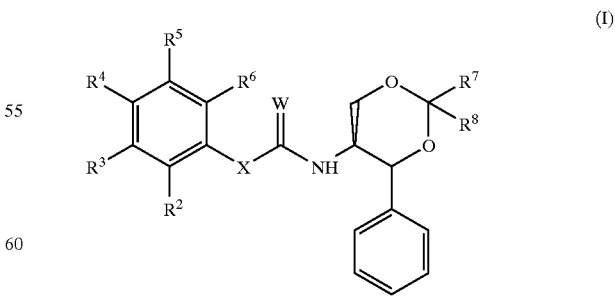

wherein:
$R^2$ is H, F, Cl, Br, I, cyano, nitro, $COR^a$, $COOR^a$, $C_{1-6}$ alkyl, $C_{1-6}$ alkoxy, $C_{1-6}$ alkylthio, $C_{1-6}$ haloalkyl, $C_{3-7}$ cycloalkyl, phenyl, $C_{2-9}$ heterocyclyl, (phenyl)-$C_{1-6}$ alkylene, ($C_{2-9}$ heterocyclyl)-$C_{1-6}$ alkylene, or ($C_{3-7}$ cycloalkyl)-$C_{1-6}$ alkylene; wherein $R^a$ is H, $C_{1-6}$ alkyl, $C_{3-7}$ cycloalkyl, or ($C_{3-7}$ cycloalkyl)-$C_{1-6}$ alkylene;

$R^3$ is H, F, Cl, Br, I, cyano, hydroxy, nitro, amino, $C_{1-6}$ alkyl, $C_{1-6}$ alkoxy, $C_{1-6}$ alkylthio, $C_{1-6}$ haloalkyl, $C_{3-7}$ cycloalkyl, phenyl, $C_{2-9}$ heterocyclyl, (phenyl)-$C_{1-6}$ alkylene, ($C_{2-9}$ heterocyclyl)-$C_{1-6}$ alkylene, or ($C_{3-7}$ cycloalkyl)-$C_{1-6}$ alkylene or $R^2$ and $R^3$ taken together with the phenyl ring to which they are attached form a naphthyl;

$R^4$ is H, F, Cl, Br, I, cyano, hydroxy, nitro, amino, $COR^b$, $COOR^b$, $C_{1-6}$ alkyl, $C_{1-6}$ alkoxy, $C_{1-6}$ alkylthio, $C_{1-6}$ haloalkyl, $C_{3-7}$ cycloalkyl, phenyl, $C_{2-9}$ heterocyclyl, (phenyl)-$C_{1-6}$ alkylene, ($C_{2-9}$ heterocyclyl)-$C_{1-6}$ alkylene, or ($C_{3-7}$ cycloalkyl)-$C_{1-6}$ alkylene; wherein $R^b$ is H, $C_{1-6}$ alkyl, $C_{3-7}$ cycloalkyl, or ($C_{3-7}$ cycloalkyl)-$C_{1-6}$ alkylene;

$R^5$ is H, F, Cl, Br, I, cyano, hydroxy, nitro, amino, $C_{1-6}$ alkyl, $C_{1-6}$ alkoxy, $C_{1-6}$ alkylthio, $C_{1-6}$ haloalkyl, or $C_{3-7}$ cycloalkyl;

$R^6$ is H, F, Cl, Br, I, cyano, hydroxy, nitro, amino, $C_{1-6}$ alkyl, $C_{1-6}$ alkoxy, $C_{1-6}$ alkylthio, $C_{1-6}$ haloalkyl, $C_{3-7}$ cycloalkyl, phenyl, $C_{2-9}$ heterocyclyl, (phenyl)-$C_{1-6}$ alkylene, ($C_{2-9}$ heterocyclyl)-$C_{1-6}$ alkylene, or ($C_{3-7}$ cycloalkyl)-$C_{1-6}$ alkylene;

X is NH, O, or $CH_2$;

W is S, O, or =N—CN;

each of $R^7$ and $R^8$ is independently selected from H, $C_{1-6}$ alkyl, $C_{3-7}$ cycloalkyl, ($C_{3-7}$ cycloalkyl)-$C_{1-6}$ alkylene, phenyl, and (phenyl)-$C_{1-6}$ alkylene, provided at least one of $R^7$ and $R^3$ is not H;

wherein each of the above hydrocarbyl or heterocarbyl moieties can be optionally substituted with between 1 and 3 substituents selected from F, Cl, Br, I, cyano, hydroxy, nitro, amino, $COR^c$, $COOR^c$, $C_{1-3}$ alkyl, $C_{1-3}$ alkoxy, $C_{1-3}$ alkylthio, $C_{1-3}$ haloalkyl, and $C_{3-6}$ cycloalkyl; wherein $R^c$ is H or $C_{1-6}$ alkyl;

provided when W is O, X is NH, and $R^7$ and $R^8$ are each methyl, and $R^3$, $R^4$, $R^5$, and $R^6$ are each H, then $R^2$ is not H, 2-chlorophenyl, or 3-quinolinyl;

and pharmaceutically acceptable salts, esters, amides, and hydrates thereof.

The invention also features a compound of formula (Ia):

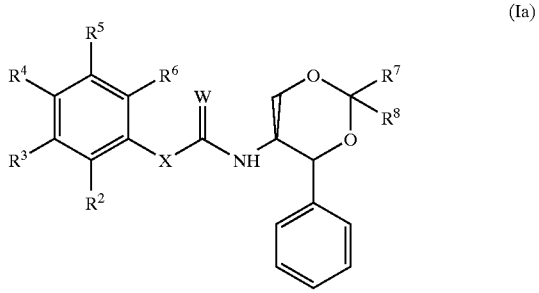

(Ia)

wherein:

R is H, F, Cl, Br, I, cyano, nitro, $COR^a$, $COOR^a$, $C_{1-6}$ alkyl, $C_{1-6}$ alkoxy, $C_{1-6}$ alkylthio, $C_{1-6}$ haloalkyl, $C_{3-7}$ cycloalkyl, phenyl, $C_{2-9}$ heterocyclyl, (phenyl)-$C_{1-6}$ alkylene, ($C_{2-9}$ heterocyclyl)-$C_{1-6}$ alkylene, or ($C_{3-7}$ cycloalkyl)-$C_{1-6}$ alkylene; wherein $R^a$ is H, $C_{1-6}$ alkyl, $C_{3-7}$ cycloalkyl, or ($C_{3-7}$ cycloalkyl)-$C_{1-6}$ alkylene;

$R^3$ is H, F, Cl, Br, I, cyano, hydroxy, nitro, amino, $C_{1-6}$ alkyl, $C_{1-6}$ alkoxy, $C_{1-6}$ alkylthio, $C_{1-6}$ haloalkyl, $C_{3-7}$ cycloalkyl, phenyl, $C_{2-9}$ heterocyclyl, (phenyl)-$C_{1-6}$ alkylene, ($C_{2-9}$ heterocyclyl)-$C_{1-6}$ alkylene, or ($C_{3-7}$ cycloalkyl)-$C_{1-6}$ alkylene or $R^2$ and $R^3$ taken together with the phenyl ring to which they are attached form a naphthyl;

$R^4$ is H, F, Cl, Br, I, cyano, hydroxy, nitro, amino, $COR^b$, $COOR^b$, $C_{1-6}$ alkyl, $C_{1-6}$ alkoxy, $C_{1-6}$ alkylthio, $C_{1-6}$ haloalkyl, $C_{3-7}$ cycloalkyl, phenyl, $C_{2-9}$ heterocyclyl, (phenyl)-$C_{1-6}$ alkylene, ($C_{2-9}$ heterocyclyl)-$C_{1-6}$ alkylene, or ($C_{3-7}$ cycloalkyl)-$C_{1-6}$ alkylene; wherein $R^b$ is H, $C_{1-6}$ alkyl, $C_{3-7}$ cycloalkyl, or ($C_{3-7}$ cycloalkyl)-$C_{1-6}$ alkylene;

$R^5$ is H, F, Cl, Br, I, cyano, hydroxy, nitro, amino, $C_{1-6}$ alkyl, $C_{1-6}$ alkoxy, $C_{1-6}$ alkylthio, $C_{1-6}$ haloalkyl, or $C_{3-7}$ cycloalkyl;

$R^6$ is H, F, Cl, Br, I, cyano, hydroxy, nitro, amino, $C_{1-6}$ alkyl, $C_{1-6}$ alkoxy, $C_{1-6}$ alkylthio, $C_{1-6}$ haloalkyl, $C_{3-7}$ cycloalkyl, phenyl, $C_{2-9}$ heterocyclyl, (phenyl)-$C_{1-6}$ alkylene, ($C_{2-9}$ heterocyclyl)-$C_{1-6}$ alkylene, or ($C_{3-7}$ cycloalkyl)-$C_{1-6}$ alkylene;

X is NH, O, or $CH_2$;

W is S, O, or =N—CN;

each of $R^7$ and $R^8$ is independently selected from H, $C_{1-6}$ alkyl, $C_{3-7}$ cycloalkyl, ($C_{3-7}$ cycloalkyl)-$C_{1-6}$ alkylene, phenyl, and (phenyl)-$C_{1-6}$ alkylene, provided at least one of $R^7$ and $R^8$ is not H;

wherein each of the above hydrocarbyl or heterocarbyl moieties can be optionally substituted with between 1 and 3 substituents selected from F, Cl, Br, I, cyano, hydroxy, nitro, amino, $COR^c$, $COOR^c$, $C_{1-3}$ alkyl, $C_{1-3}$ alkoxy, $C_{1-3}$ alkylthio, $C_{1-3}$ haloalkyl, and $C_{3-6}$ cycloalkyl; wherein $R^c$ is H or $C_{1-6}$ alkyl;

provided when W is O, X is NH, and $R^7$ and $R^8$ are each methyl, and $R^3$, $R^4$, $R^5$, and $R^6$ are each H, then $R^2$ is not H, Br, phenyl, 2-chlorophenyl, or 3-quinolinyl;

provided when W is O, X is NH, and $R^7$ and $R^8$ are each methyl, and $R^4$, $R^5$, and $R^6$ are each H, then $R^3$ is not Cl nor is $R^3$ taken together with $R^2$; and provided when W is O, X is NH, and $R^7$ and $R^8$ are each methyl, and $R^2$, $R^5$, and $R^6$ are each H, then $R^4$ is not Cl;

or a pharmaceutically acceptable salt, amide, or ester thereof; or a stereoisomeric form thereof.

The disclosed compounds are inhibitors of the orexin-2 receptor, and preferably, selective inhibitors. For use in medicine, the preparation of pharmaceutically acceptable salts of compounds of formula (I) may be desirable.

Certain compounds of the present invention may have one stereogenic atom and may exist as two enantiomers. Certain compounds of the present invention may have two or more stereogenic atoms and may further exist as diastereomers. It is to be understood by those skilled in the art that all such stereoisomers and mixtures thereof in any proportion are encompassed within the scope of the present invention.

Another aspect of the invention provides pharmaceutical compositions comprising a compound of formula (I) and a pharmaceutically acceptable carrier. A further embodiment of the invention is a process for making a pharmaceutical composition comprising mixing a disclosed compound as described above, with a suitable pharmaceutically acceptable carrier.

The invention also contemplates pharmaceutical compositions comprising more than one compound of formula (I) and compositions comprising a compound of formula (I) and another pharmaceutically active agent.

The invention features a method of treating disorders or conditions mediated by the orexin-2 receptor, in a subject in need thereof, comprising administering to the subject a therapeutically effective amount of any of the compounds or pharmaceutical compositions described above. The compounds described herein inhibit the activity of orexin-2 receptor, which modulates functions such as feeding, drinking, arousal, stress, metabolism and reproduction. In preferred embodiments, orexin-2 receptor inhibition is selective. As such, the disclosed compounds and compositions are useful in the prevention, inhibition, or treatment of sleep-wake transition disorders, insomnia, restless legs syndrome, jet-lag, sleep disorders secondary to neurological disorders (manias, depressions, manic depression, schizophrenia, pain syndromes and the like), Parkinson's Disease, Gilles de la Tourette's Syndrome, anxiety, delirium, dementias, obesity (and may, through weight loss, be useful to treat consequences of obesity such as insulin resistance/ type 2 diabetes, hyperlipidemia, gallstones, angina, high blood pressure, breathlessness, infertility, sleep apnea, back pain, joint pain, varicose veins and osteoarthritis), ulcers, irritable bowel syndrome, diarrhea, gastroesophageal reflux, hypertension, angina pectoris, arrhythmias, tachycardia, and acute heart failure.

Additional features and advantages of the invention will become apparent from the detailed description below, including examples, and the appended claims.

DETAILED DESCRIPTION OF THE INVENTION

The invention features urea compounds of formula (I), methods of making them, compositions containing them, and methods of using them to treat diseases and conditions, including those mediated by orexin-2.

A. Terms

The following terms are defined below and by their usage throughout this disclosure.

"Alkyl" includes optionally substituted straight chain and branched hydrocarbons with at least one hydrogen removed to form a radical group. Alkyl groups include methyl, ethyl, propyl, isopropyl, butyl, isobutyl, t-butyl, 1-methylpropyl, pentyl, isopentyl, sec-pentyl, hexyl, heptyl, octyl, and so on. Alkyl includes cycloalkyl, such as cyclopropyl, cyclobutyl, cyclopentyl, and cyclohexyl.

"Alkenyl" includes optionally substituted straight chain and branched hydrocarbon radicals as above with at least one carbon-carbon double bond ($Sp^2$). Alkenyls include ethenyl (or vinyl), prop-1-enyl, prop-2-enyl (or allyl), isopropenyl (or 1-methylvinyl), but-1-enyl, but-2-enyl, butadienyls, pentenyls, hexa-2,4-dienyl, and so on. Hydrocarbon radicals having a mixture of double bonds and triple bonds, such as 2-penten-4-ynyl, are grouped as alkynyls herein. Alkenyl includes cycloalkenyl. Cis and trans or (E) and (Z) forms are included within the invention.

"Alkynyl" includes optionally substituted straight chain and branched hydrocarbon radicals as above with at least one carbon-carbon triple bond (sp). Alkynyls include ethynyl, propynyls, butynyls, and pentynyls. Hydrocarbon radicals having a mixture of double bonds and triple bonds, such as 2-penten-4-ynyl, are grouped as alkynyls herein. Alkynyl does not include cycloalkynyl.

"Alkoxy" includes an optionally substituted straight chain or branched alkyl group with a terminal oxygen linking the alkyl group to the rest of the molecule. Alkoxy includes methoxy, ethoxy, propoxy, isopropoxy, butoxy, t-butoxy, pentoxy and so on. "Aminoalkyl", "thioalkyl", and "sulfonylalkyl" are analogous to alkoxy, replacing the terminal oxygen atom of alkoxy with, respectively, NH (or NR), S, and $SO_2$. Heteroalkyl includes alkoxy, aminoalkyl, thioalkyl, and so on.

"Aryl" includes phenyl, naphthyl, biphenylyl, tetrahydronaphthyl, and so on, any of which may be optionally substituted. Aryl also includes arylalkyl groups such as benzyl, phenethyl, and phenylpropyl. Aryl includes a ring system containing an optionally substituted 6-membered carbocyclic aromatic ring, said system may be bicyclic, bridge, and/or fused. The system may include rings that are aromatic, or partially or completely saturated. Examples of ring systems include indenyl, pentalenyl, 1-4-dihydronaphthyl, indanyl, benzimidazolyl, benzothiophenyl, indolyl, benzofuranyl, isoquinolinyl, and so on.

"Heterocyclyl" includes optionally substituted aromatic and nonaromatic rings having carbon atoms and at least one heteroatom (O, S, N) or heteroatom moiety ($SO_2$, CO, CONH, COO) in the ring. Unless otherwise indicated, a heterocyclic radical may have a valence connecting it to the rest of the molecule through a carbon atom, such as 3-furyl or 2-imidazolyl, or through a heteroatom, such as N-piperidyl or 1-pyrazolyl. Preferably a monocyclic heterocyclyl has between 4 and 7 ring atoms, or between 5 and 6 ring atoms; there may be between 1 and 5 heteroatoms or heteroatom moieties in the ring, and preferably between 1 and 3. A heterocyclyl may be saturated, unsaturated, aromatic (e.g., heteroaryl), nonaromatic, or fused.

Heterocyclyl also includes fused, e.g., bicyclic, rings, such as those optionally condensed with an optionally substituted carbocyclic or heterocyclic five- or six-membered aromatic ring. For example, "heteroaryl" includes an optionally substituted six-membered heteroaromatic ring containing 1, 2 or 3 nitrogen atoms condensed with an optionally substituted five- or six-membered carbocyclic or heterocyclic aromatic ring. Said heterocyclic five- or six-membered aromatic ring condensed with the said five- or six-membered aromatic ring may contain 1, 2 or 3 nitrogen atoms where it is a six-membered ring, or 1, 2 or 3 heteroatoms selected from oxygen, nitrogen and sulfur where it is a five-membered ring.

Examples of heterocyclyls include thiazoylyl, furyl, pyranyl, isobenzofuranyl, pyrrolyl, imidazolyl, pyrazolyl, isothiazolyl, isoxazolyl, pyridyl, pyrazinyl, pyrimidinyl, pyridazinyl, indolizinyl, isoindolyl, indolyl, indazolyl, purinyl, quinolyl, furazanyl, pyrrolidinyl, pyrrolinyl, imdazolidinyl, imidazolinyl, pyrazolidinyl, pyrazolinyl, piperidyl, piperazinyl, indolinyl, and morpholinyl. For example, preferred heterocyclyls or heterocyclic radicals include morpholinyl, piperazinyl, pyrrolidinyl, pyridyl, cyclohexylimino, cycloheptylimino, and more preferably, piperidyl.

Examples illustrating heteroaryl are thienyl, furanyl, pyrrolyl, imidazolyl, oxazolyl, thiazolyl, benzothienyl, benzofuranyl, benzimidazolyl, benzoxazolyl, and benzothiazolyl.

"Acyl" refers to a carbonyl moiety attached to either a hydrogen atom (i.e., a formyl group) or to an optionally substituted alkyl or alkenyl chain, or heterocyclyl.

"Halo" or "halogen" includes fluoro, chloro, bromo, and iodo, and preferably chloro, bromo, or iodo as a substituent.

"Alkanediyl" or "alkylene" represents straight or branched chain optionally substituted bivalent alkane radicals such as, for example, methylene, ethylene, propylene, butylene, pentylene or hexylene.

"Alkenediyl" represents, analogous to the above, straight or branched chain optionally substituted bivalent alkene radicals such as, for example, propenylene, butenylene, pentenylene or hexenylene. In such radicals, the carbon atom linking a nitrogen preferably should not be unsaturated.

"Aroyl" refers to a carbonyl moiety attached to an optionally substituted aryl or heteroaryl group, wherein aryl and heteroaryl have the definitions provided above. In particular, benzoyl is phenylcarbonyl.

As defined herein, two radicals, together with the atom(s) to which they are attached may form an optionally substituted 4- to 7-, 5- to 7-, or a 5- to 6-membered ring carbocyclic or heterocyclic ring, which ring may be saturated, unsaturated or aromatic. Said rings may be as defined above in the Summary of the Invention section. Particular examples of such rings are as follows in the next section.

"Pharmaceutically acceptable salts, esters, and amides" include carboxylate salts (e.g., $C_{1-8}$ alkyl, cycloalkyl, aryl, heteroaryl, or non-aromatic heterocyclic) amino acid addition salts, esters, and amides that are within a reasonable benefit/risk ratio, pharmacologically effective and suitable for contact with the tissues of patients without undue toxicity, irritation, or allergic response. Representative salts include hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, and laurylsulfonate. These may include alkali metal and alkali earth cations such as sodium, potassium, calcium, and magnesium, as well as non-toxic ammonium, quaternary ammonium, and amine cations such as tetramethyl ammonium, methylamine, trimethylamine, and ethylamine. See, for example, S. M. Berge, et al., "Pharmaceutical Salts," J. Pharm. Sci., 1977, 66:1–19, which is incorporated herein by reference. Representative pharmaceutically acceptable amides of the invention include those derived from ammonia, primary $C_{1-6}$ alkyl amines and secondary di($C_{1-6}$ alkyl)amines. Secondary amines include 5- or 6-membered heterocyclic or heteroaromatic ring moieties containing at least one nitrogen atom and optionally between 1 and 2 additional heteroatoms. Preferred amides are derived from ammonia, $C_{1-3}$ alkyl primary amines, and di ($C_{1-2}$ alkyl)amines. Representative pharmaceutically acceptable esters of the invention include $C_{1-7}$ alkyl, $C_{5-7}$ cycloalkyl, phenyl, and phenyl($C_{1-6}$)alkyl esters. Preferred esters include methyl esters.

"Patient" or "subject" includes mammals such as humans and animals (dogs, cats, horses, rats, rabbits, mice, non-human primates) in need of observation, experiment, treatment or prevention in connection with the relevant disease or condition. Preferably, the patient or subject is a human.

"Composition" includes a product comprising the specified ingredients in the specified amounts as well as any product that results directly or indirectly from combinations of the specified ingredients in the specified amounts.

"Therapeutically effective amount" or "effective amount" means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

Concerning the various radicals in this disclosure and in the claims, three general remarks are made. The first remark concerns valency. As with all hydrocarbon radicals, whether saturated, unsaturated or aromatic, and whether or not cyclic, straight chain, or branched, and also similarly with all heterocyclic radicals, each radical includes substituted radicals of that type and monovalent, bivalent, and multivalent radicals as indicated by the context of the claims. The context will indicate that the substituent is an alkylene or hydrocarbon radical with at least two hydrogen atoms removed (bivalent) or more hydrogen atoms removed (multivalent). An example of a bivalent radical linking two parts of the molecule is X in formula (I) that links a substituted phenyl.

Second, radicals or structure fragments as defined herein are understood to include substituted radicals or structure fragments. Hydrocarbyls include monovalent radicals containing carbon and hydrogen such as alkyl, alkenyl, alkynyl, cycloalkyl, and cycloalkenyl (whether aromatic or unsaturated), as well as corresponding divalent radicals such as alkylene, alkenylene, phenylene, and so on. Heterocarbyls include monovalent and divalent radicals containing carbon, hydrogen, and at least one heteroatom. Examples of monovalent heterocarbyls include acyl, acyloxy, alkoxyacyl, heterocyclyl, heteroaryl, aroyl, benzoyl, dialkylamino, hydroxyalkyl, and so on. Using "alkyl" as an example, "alkyl" should be understood to include substituted alkyl having one or more substitutions, such as between 1 and 5, 1 and 3, or 2 and 4 substituents. The substituents may be the same (dihydroxy, dimethyl), similar (chlorofluoro), or different (chlorobenzyl- or aminomethyl-substituted). Examples of substituted alkyl include haloalkyl (such as fluoromethyl, chloromethyl, difluoromethyl, perchloromethyl, 2-bromoethyl, perfluoromethyl, and 3-iodocyclopentyl), hydroxyalkyl (such as hydroxymethyl, hydroxyethyl, 2-hydroxypropyl, aminoalkyl (such as aminomethyl, 2-aminoethyl, 3-aminopropyl, and 2-aminopropyl), nitroalkyl, alkylalkyl, and so on. A di($C_{1-6}$ alkyl)amino group includes independently selected alkyl groups, to form, for example, methylpropylamino and isopropylmethylamino, in addition dialkylamino groups having two of the same alkyl group such as dimethyl amino or diethylamino.

Third, only stable compounds are intended. For example, where there is an NR'R" group, and R can be an alkenyl group, the double bond is at least one carbon removed from the nitrogen to avoid enamine formation. Similarly, where a dashed line is an optional sp2 bond, if it is absent, the appropriate hydrogen atom(s) is (are) included.

Preferred substitution patterns for Ar are 2-substituted 2,4-disubstituted phenyl and 2,5-disubstituted phenyl. Compounds of the invention are further described in the next section.

B. Compounds

The invention features compounds of formula (I) as described in the Summary section.

Preferred compounds include those wherein: (a) W is O; (b) $R^2$ and $R^4$ are not hydrogen, and preferably are alkyl or halo; (c) X is $CH_2$; (d) X is NH; (e) each of $R^7$ and $R^8$ is independently selected from methyl, ethyl, and propyl; (f) at least two of $R^3$, $R^5$, and $R^6$ are H; (g) $R^2$ is H, Cl, Br, I, methyl, halomethyl, cyano, amino, $C_{2-9}$ heterocyclyl, phenyl, or phenyl substituted with hydroxy, thiol, nitro, cyano, or halo; (h) $R^2$ is Cl, Br, I, methyl, cyano, $C_{2-9}$ heteroaryl, phenyl, or phenyl substituted with hydroxy, thiol, or halo; (i) $R^3$ is H or methyl; (u) $R^3$ is H; (k) $R^4$ is H, Cl, Br, I, methyl, halomethyl, cyano, amino, $C_{2-9}$ heterocyclyl, phenyl, or phenyl substituted with hydroxy, thiol, nitro, cyano, or halo; (l) $R^4$ is H, Cl, Br, I, or methyl; (m) $R^5$ is H, Cl, Br, I, methyl, halomethyl, methoxy, thiomethyl, ethyl, ethoxy, or thioethyl; (n) $R^5$ is H, methyl, or Cl; (o) the stereochemistry of the two dioxane chiral centers is (S,S); (p) $R^3$ is not Cl; (q) $R^3$ is not halo;

(r) $R^5$ is not Cl; (s) $R^5$ is not halo; (t) $R^2$ and $R^3$ are not both chloro; (u) $R^2$ and $R^3$ are not both halo; (v) $R^3$ and $R^4$ are not both chloro; (w) $R^3$ and $R^4$ are not both halo; (x) said compound is selective for inhibiting human orexin-2 over human orexin-1 by a factor of at least 10; (y) said compound is selective for inhibiting human orexin-2 over human orexin-1 by a factor of at least 100; (z) or combinations of the above.

Examples of preferred compounds also include:
1-(4-Bromo-2-chloro-phenyl)-3-((4S,5S)-2,2-dimethyl-4-phenyl-[1,3]dioxan-5-yl)-urea;
1-(2,4-Dibromo-phenyl)-3-((4S,5S)-2,2-dimethyl-4-phenyl-[1,3]dioxan-5-yl)-urea;
1-(2,4-Dichloro-phenyl)-3-((4S,5S)-2,2-dimethyl-4-phenyl-[1,3]dioxan-5-yl)-urea;
1-(2-Chloro-5-methyl-phenyl)-3-((4S,5S)-2,2-dimethyl-4-phenyl-[1,3]dioxan-5-yl)-urea;
1-((4S,5S)-2,2-Dimethyl-4-phenyl-[1,3]dioxan-5-yl)-3-(2-thiophen-2-yl-phenyl)-urea;
1-((4S,5S)-2,2-Dimethyl-4-phenyl-[1,3]dioxan-5-yl)-3-(2-iodo-phenyl)-urea;
1-((4S,5S)-2,2-Dimethyl-4-phenyl-[1,3]dioxan-5-yl)-3-(4-iodo-phenyl)-urea;
1-(4-Bromo-2-methyl-phenyl)-3-((4S,5S)-2,2-dimethyl-4-phenyl-[1,3]dioxan-5-yl)-urea;
1-(2-Bromo-4-methyl-phenyl)-3-((4S,5S)-2,2-dimethyl-4-phenyl-[1,3]dioxan-5-yl)-urea;
1-(2-Cyano-phenyl)-3-((4S,5S)-2,2-dimethyl-4-phenyl-[1,3]dioxan-5-yl)-urea;
1-(3'-Chloro-biphenyl-2-y)-3-((4S,5S)-2,2-dimethyl-4-phenyl-[1,3]dioxan-5-yl)-urea;
1-(2,5-Dimethyl-phenyl)-3-((4S,5S)-2,2-dimethyl-4-phenyl-[1,3]dioxan-5-yl)-urea;
1-Biphenyl-2-yl-3-((4S,5S)-2,2-dimethyl-4-phenyl-[1,3]dioxan-5-yl)-urea;
1-((4S,5S)-2,2-Dimethyl-4-phenyl-[1,3]dioxan-5-yl)-3-(2-trifluoromethyl-phenyl)-urea;
1-(4-Bromo-3-methyl-phenyl)-3-((4S,5S)-2,2-dimethyl-4-phenyl-[1,3]dioxan-5-yl)-urea;
1-(2-Bromo-phenyl)-3-((4S,5S)-2,2-dimethyl-4-phenyl-[1,3]dioxan-5-yl)-urea;
1-(2,5-Dichloro-phenyl)-3-((4S,5S)-2,2-dimethyl-4-phenyl-[1,3]dioxan-5-yl)-urea;
1-(2-Chloro-5-trifluoromethyl-phenyl)-3-((4S,5S)-2,2-dimethyl-4-phenyl-[1,3]dioxan-5-yl)-urea;
1-(2-Bromo-phenyl)-3-((4R,5S)-2,2-dimethyl-4-phenyl-[1,3]dioxan-5-yl)-urea; and
1-((4S,5S)-2,2-Dimethyl-4-phenyl-[1,3]dioxan-5-yl)-3-(2-thiophen-3-yl-phenyl)-urea.

The most preferred compounds are:
1-(4-Bromo-2-chloro-phenyl)-3-((4S,5S)-2,2-dimethyl-4-phenyl-[1,3]dioxan-5-yl)-urea;
1-(2,4-Dibromo-phenyl)-3-((4S,5S)-2,2-dimethyl-4-phenyl-[1,3]dioxan-5-yl)-urea;
1-(2,4-Dichloro-phenyl)-3-((4S,5S)-2,2-dimethyl-4-phenyl-[1,3]dioxan-5-yl)-urea; and
1-(2-Bromo-4-methyl-phenyl)-3-((4S,5S)-2,2-dimethyl-4-phenyl-[1,3]dioxan-5-yl)-urea.

Additional compounds of the invention include:
1-((4S,5S)-2,2-Dimethyl-4-phenyl-[1,3]dioxan-5-yl)-3-(2-phenoxy-phenyl)-urea;
1-(2,4-Dichloro-phenyl)-3-((4S,5S)-2,2-dimethyl-4-phenyl-[1,3]dioxan-5-yl)-thiourea;
1-((4S,5S)-2,2-Dimethyl-4-phenyl-[1,3]dioxan-5-yl)-3-(2-pyridin-3-yl-phenyl)-urea;
1-(2-Bromo-phenyl)-3-((4S,5S)-2,2-dimethyl-4-phenyl-[1,3]dioxan-5-yl)-thiourea;
1-(2,4-Dibromo-phenyl)-3-((2S,3S)-2-phenyl-1,5-dioxa-spiro[5.5]undec-3-yl)-urea;
1-(2-Bromo-phenyl)-3-((2S,3S)-2-phenyl-1,5-dioxa-spiro[5.5]undec-3-yl)-urea;
N-(2-Bromo-4-methyl-phenyl)-N'-((4S,5S)-2,2-dimethyl-4-phenyl-[1,3]dioxan-5-yl)-N"-cyanoguanidine;
1-(2-Bromo-phenyl)-3-((4S,5S)-2-methyl-2,4-diphenyl-[1,3]dioxan-5-yl)-urea;
1-((4S,5S)-2,2-Dimethyl-4-phenyl-[1,3]dioxan-5-yl)-3-(4-pyridin-3-yl-phenyl)-urea; and
1-((4S,5S)-2,2-Dimethyl-4-phenyl-[1,3]dioxan-5-yl)-3-phenyl-urea.

Additional examples of compounds of the invention include:
1-(2,4-Dimethyl-phenyl)-3-((4S,5S)-2,2-dimethyl-4-phenyl-[1,3]dioxan-5-yl)-urea;
1-(2-Chloro-phenyl)-3-((4S,5S)-2,2-dimethyl-4-phenyl-[1,3]dioxan-5-yl)-urea;
1-((4S,5S)-2,2-Dimethyl-4-phenyl-[1,3]dioxan-5-yl)-3-(2-fluoro-phenyl)-urea;
1-((4S,5S)-2,2-Dimethyl-4-phenyl-[1,3]dioxan-5-yl)-3-o-tolyl-urea;
1-((4S,5S)-2,2-Dimethyl-4-phenyl-[1,3]dioxan-5-yl)-3-(2-nitro-phenyl)-urea;
2-(2-Bromo-phenyl)-N-((4S,5S)-2,2-dimethyl-4-phenyl-[1,3]dioxan-5-yl)-acetamide;
((4S,5S)-2,2-Dimethyl-4-phenyl-[1,3]dioxan-5-yl)-carbamic acid 2-chloro-phenyl ester;
1-(4-Bromo-phenyl)-3-((4S,5S)-2,2-dimethyl-4-phenyl-[1,3]dioxan-5-yl)-urea;
1-((4S,5S)-2,2-Dimethyl-4-phenyl-[1,3]dioxan-5-yl)-3-(2-methoxy-phenyl)-urea;
1-(4-Chloro-phenyl)-3-((4S,5S)-2,2-dimethyl-4-phenyl-[1,3]dioxan-5-yl)-urea;
2-[3-((4S,5S)-2,2-Dimethyl-4-phenyl-[1,3]dioxan-5-yl)-ureido]-benzoic acid;
2-[3-((4S,5S)-2,2-Dimethyl-4-phenyl-[1,3]dioxan-5-yl)-ureido]-benzoic acid methyl ester;
1-((4S,5S)-2,2-Dimethyl-4-phenyl-[1,3]dioxan-5-yl)-3-(2-isopropyl-phenyl)-urea;
1-(2,6-Dichloro-phenyl)-3-((4S,5S)-2,2-dimethyl-4-phenyl-[1,3]dioxan-5-yl)-urea;
1-(3-Bromo-phenyl)-3-((4S,5S)-2,2-dimethyl-4-phenyl-[1,3]dioxan-5-yl)-urea;
1-(2,4-Difluoro-phenyl)-3-((4S,5S)-2,2-dimethyl-4-phenyl-[1,3]dioxan-5-yl)-urea; and
1-(3-Chloro-phenyl)-3-((4S,5S)-2,2-dimethyl-4-phenyl-[1,3]dioxan-5-yl)-urea.

Additional compounds of the invention include:
1-(2-Chloro-4-methylphenyl)-((4S,5S)-2,2-dimethyl-4-phenyl[1,3]dioxan-5-yl)-urea;
1-(2-Iodo-4-methylphenyl)-((4S,5S)-2,2-dimethyl-4-phenyl[1,3]dioxan-5-yl)-urea;
1-(4-chloro-2-methylphenyl)-((4S,5S)-2,2-dimethyl-4-phenyl[1,3]dioxan-5-yl)-urea;
1-(4-iodo-2-methylphenyl)-((4S,5S)-2,2-dimethyl-4-phenyl[1,3]dioxan-5-yl)-urea; and
1-(2-Bromo-5-methylphenyl)-((4S,5S)-2,2-dimethyl-4-phenyl[1,3]dioxan-5-yl)-urea.

Related Compounds

The invention provides the disclosed compounds and closely related, pharmaceutically acceptable forms of the disclosed compounds, such as salts, esters, amides, acids, hydrates or solvated forms thereof; masked or protected forms; and racemic mixtures, or enantiomerically or optically pure forms. Related compounds also include compounds of the invention that have been modified to be detectable, e.g., isotopically labelled with $^{18}F$, $^{15}O$, $^{13}N$ or $^{11}C$ for use as a probe in positron emission tomography (PET) or single-photon emission computed tomography (SPECT).

The invention also includes disclosed compounds having one or more functional groups (e.g., hydroxyl, amino, or carboxyl) masked by a protecting group. See, e.g., Greene and Wuts, *Protective Groups in Organic Synthesis*, 3$^{rd}$ ed., (1999) John Wiley & Sons, NY. Some of these masked or protected compounds are pharmaceutically acceptable; others will be useful as intermediates. Synthetic intermediates and processes disclosed herein, and minor modifications thereof, are also within the scope of the invention.

Hydroxyl Protecting Groups

Protection for the hydroxyl group includes methyl ethers, substituted methyl ethers, substituted ethyl ethers, substitute benzyl ethers, and silyl ethers.

Substituted Methyl Ethers

Examples of substituted methyl ethers include methyoxymethyl, methylthiomethyl, t-butylthiomethyl, (phenyldimethylsilyl)methoxymethyl, benzyloxymethyl, p-methoxybenzyloxymethyl, (4-methoxyphenoxy)methyl, guaiacolmethyl, t-butoxymethyl, 4-pentenyloxymethyl, siloxymethyl, 2-methoxyethoxymethyl, 2,2,2-trichloroethoxymethyl, bis(2-chloroethoxy)methyl, 2-(trimethylsilyl)ethoxymethyl, tetrahydropyranyl, 3-bromotetrahydropyranyl, tetrahydrothiopyranyl, 1-methoxycyclohexyl, 4-methoxytetrahydropyranyl, 4-methoxytetrahydrothiopyranyl, 4-methoxytetrahydrothiopyranyl S,S-dioxido, 1-[(2-chloro-4-methyl)phenyl]4-methoxypiperidin4-yl, 1,4-dioxan-2-yl, tetrahydrofuranyl, tetrahydrothiofuranyl and 2,3,3a,4,5,6,7, 7a-octahydro-7,8,8-trimethyl-4,7-methanobenzofuran-2-yl.

Substituted Ethyl Ethers

Examples of substituted ethyl ethers include 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, and benzyl.

Substituted Benzyl Ethers

Examples of substituted benzyl ethers include p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2- and 4-picolyl, 3-methyl-2-picolyl N-oxido, diphenylmethyl, p, p'-dinitrobenzhydryl, 5-dibenzosuberyl, triphenylmethyl, α-naphthyldiphenylmethyl, p-methoxyphenyldiphenylmethyl, di(p-methoxyphenyl) phenylmethyl, tri(p-methoxyphenyl)methyl, 4-(4'-bromophenacyloxy)phenyldiphenylmethyl, 4,4',4"-tris(4,5-dichlorophthalimidophenyl)methyl, 4,4',4"-tris (levulinoyloxyphenyl)methyl, 4,4',4"-tris (benzoyloxyphenyl)methyl, 3-(Imidazol-1-ylmethyl)bis(4', 4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, and benzisothiazolyl S,S-dioxido.

Silyl Ethers

Examples of silyl ethers include trimethylsilyl, triethylsilyl, triisopropylsilyl, dimethylisopropylsilyl, diethylisopropylsilyl, dimethylthexylsilyl, t-butyldimethylsilyl, t-butyldiphenylsilyl, tribenzylsilyl, tri-p-xylylsilyl, triphenylsilyl, diphenylmethylsilyl, and t-butylmethoxyphenylsilyl.

Esters

In addition to ethers, a hydroxyl group may be protected as an ester. Examples of esters include formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, p-P-phenylacetate, 3-phenylpropionate, 4-oxopentanoate(levulinate), 4,4-(ethylenedithio)pentanoate, pivaloate, adamantoate, crotonate, 4-methoxycrotonate, benzoate, p-phenylbenzoate, and 2,4,6-trimethylbenzoate(mesitoate).

Carbonates

Examples of carbonate protecting groups include methyl, 9-fluorenylmethyl, ethyl, 2,2,2-trichloroethyl, 2-(trimethylsilyl)ethyl, 2-(phenylsulfonyl)ethyl, 2-(triphenylphosphonio)ethyl, isobutyl, vinyl, allyl, p-nitrophenyl, benzyl, p-methoxybenzyl, 3,4-dimethoxybenzyl, o-nitrobenzyl, p-nitrobenzyl, S-benzyl thiocarbonate, 4-ethoxy-1-naphthyl, and methyl dithiocarbonate.

Assisted Cleavage

Examples of assisted cleavage include 2-iodobenzoate, 4-azidobutyrate, 4-nitro-4-methylpentanoate, o-(dibromomethyl)benzoate, 2-formylbenzenesulfonate, 2-(methylthiomethoxy)ethyl carbonate, 4-(methylthiomethoxy)butyrate, and 2-(methylthiomethoxymethyl)benzoate.

Miscellaneous Esters

Examples of miscellaneous esters include 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate (tigloate), o-(methoxycarbonyl)benzoate, p-P-benzoate, α-naphthoate, nitrate, alkyl N,N,N',N'-tetramethylphosphorodiamidate, N-phenylcarbamate, borate, dimethylphosphinothioyl, and 2,4-dinitrophenylsulfenate.

Sulfonates

Examples of sulfonates include sulfate, methanesulfonate (mesylate), benzylsulfonate, and tosylate.

Amino Protecting Groups

Protection for the amino group includes carbamates, amides, and special —NH protective groups.

Examples of carbamates include methyl and ethyl carbamates, substituted ethyl carbamates, assisted cleavage carbamates, photolytic cleavage carbamates, urea-type derivatives, and miscellaneous carbamates.

Carbamates

Examples of methyl and ethyl carbamates include methyl and ethyl, 9-fluorenylmethyl, 9-(2-sulfo)fluorenylmethyl, 9-(2,7-dibromo)fluorenylmethyl, 2,7-di-t-butyl-[9-(10,10-dioxo-10,10,10,10-tetrahydrothioxanthyl)]methyl, and 4-methoxyphenacyl.

Substituted Ethyl

Examples of substituted ethyl carbamates include 2,2,2-trichloroethyl, 2-trimethylsilylethyl, 2-phenylethyl, 1-(1-adamantyl)-1-methylethyl, 1,1-dimethyl-2-haloethyl, 1,1-dimethyl-2,2-dibromoethyl, 1,1-dimethyl-2,2,2-trichloroethyl, 1-methyl-1-(4-biphenylyl)ethyl, 1-(3,5-di-t-butylphenyl)-1-methylethyl, 2-(2'- and 4'-pyridyl)ethyl, 2-(N,N-dicyclohexylcarboxamido)ethyl, t-butyl, 1-adamantyl, vinyl, allyl, 1-isopropylallyl, cinnamyl, 4-nitrocinnamyl, 8-quinolyl, N-hydroxypiperidinyl, alkyldithio, benzyl, p-methoxybenzyl, p-nitrobenzyl, p-bromobenzyl, p-chlorobenzyl, 2,4-dichlorobenzyl, 4-methylsulfinylbenzyl, 9-anthrylmethyl, and diphenylmethyl.

Assisted Cleavage

Examples of assisted cleavage include 2-methylthioethyl, 2-methylsulfonylethyl, 2-(p-toluenesulfonyl)ethyl, [2-(1,3-dithianyl)]methyl, 4-methylthiophenyl, 2,4- dimethylthiophenyl, 2-phosphonioethyl, 2-triphenylphosphonioisopropyl, 1,1-dimethyl-2-cyanoethyl, m-chloro-p-acyloxybenzyl, p-(dihydroxyboryl)benzyl, 5-benzisoxazolylmethyl, and 2-(trifluoromethyl)-6-chromonylmethyl.

Photolytic Cleavage

Examples of photolytic cleavage include m-nitrophenyl, 3,5-dimethoxybenzyl, o-nitrobenzyl, 3,4-dimethoxy-6-nitrobenzyl, and phenyl(o-nitrophenyl)methyl.

Urea-type Derivatives

Examples of urea-type derivatives include phenothiazinyl-(10)-carbonyl derivative, N'-p-toluenesulfonylaminocarbonyl, and N'-phenylaminothiocarbonyl.

Miscellaneous Carbamates

Examples of miscellaneous carbamates include t-amyl, S-benzyl thiocarbamate, p-cyanobenzyl, cyclobutyl, cyclohexyl, cyclopentyl, cyclopropylmethyl, p-decyloxybenzyl, diisopropylmethyl, 2,2-dimethoxycarbonylvinyl, o-(N,N-dimethylcarboxamido)benzyl, 1,1-dimethyl-3-(N,N-dimethylcarboxamido)propyl, 1,1-dimethylpropynyl, di(2-pyridyl)methyl, 2-furanylmethyl, 2-iodoethyl, isobornyl, isobutyl, isonicotinyl, p-(p'-methoxyphenylazo)benzyl, 1-methylcyclobutyl, 1-methylcyclohexyl, 1-methyl-1-cyclopropylmethyl, 1-methyl-1-(3,5-dimethoxyphenyl)ethyl, 1-methyl-1-(p-phenylazophenyl)ethyl, 1-methyl-1-phenylethyl, 1-methyl-1-(4-pyridyl)ethyl, phenyl, p-(phenylazo)benzyl, 2,4,6-tri-t-butylphenyl, 4-(trimethylammonium)benzyl, and 2,4,6-trimethylbenzyl.

Examples of Amides Include:

Amides

N-formyl, N-acetyl, N-chloroacetyl, N-trichloroacetyl, N-trifluoroacetyl, N-phenylacetyl, N-3-phenylpropionyl, N-picolinoyl, N-3-pyridylcarboxamide, N-benzoylphenylalanyl derivative, N-benzoyl, and N-p-phenylbenzoyl.

Assisted Cleavage

N-o-nitrophenylacetyl, N-o-nitrophenoxyacetyl, N-acetoacetyl, (N'-dithiobenzyloxycarbonylamino)acetyl, N-3-(p-hydroxyphenyl)propionyl, N-3-(o-nitrophenyl)propionyl, N-2-methyl-2-(o-nitrophenoxy)propionyl, N-2-methyl-2-(o-phenylazophenoxy)propionyl, N-4-chlorobutyryl, N-3-methyl-3-nitrobutyryl, N-o-nitrocinnamoyl, N-acetylmethionine derivative, N-o-nitrobenzoyl, N-o-(benzoyloxymethyl)benzoyl, and 4,5-diphenyl-3-oxazolin-2-one.

Cyclic Imide Derivatives

N-phthalimide, N-dithiasuccinoyl, N-2,3-diphenylmaleoyl, N-2,5-dimethylpyrrolyl, N-1, 1,4,4-tetramethyldisilylazacyclopentane adduct, 5-substituted 1,3-dimethyl-1,3,5-triazacyclohexan-2-one, 5-substituted 1,3-dibenzyl-1,3,5-triazacyclohexan-2-one, and 1-substituted 3,5-dinitro-4-pyridonyl.

Special—NH Protective Groups

Examples of Special NH Protective Groups Include:

N-Alkyl and N-Aryl Amines

N-methyl, N-allyl, N-[2-(trimethylsilyl)ethoxy]methyl, N-3-acetoxypropyl, N-(1-isopropyl-4-nitro-2-oxo-3-pyrrolin-3-yl), quaternary ammonium salts, N-benzyl, N-di(4-methoxyphenyl)methyl, N-5-dibenzosuberyl, N-triphenylmethyl, N-(4-methoxyphenyl)diphenylmethyl, N-9-phenylfluorenyl, N-2,7-dichloro-9-fluorenylmethylene, N-ferrocenylmethyl, and N-2-picolylamine N'-oxide.

Imine Derivatives

N-1,1-dimethylthiomethylene, N-benzylidene, N-p-methoxybenzylidene, N-diphenylmethylene, N-[(2-pyridyl)mesityl]methylene, and N-(N',N'-dimethylaminomethylene).

Protection for the Carbonyl Group

Acyclic Acetals and Ketals

Examples of acyclic acetals and ketals include dimethyl, bis(2,2,2-trichloroethyl), dibenzyl, bis(2-nitrobenzyl), and diacetyl.

Cyclic Acetals and Ketals

Examples of cyclic acetals and ketals include 1,3-dioxanes, 5-methylene-1,3-dioxane, 5,5-dibromo-1,3-dioxane, 5-(2-pyridyl)-1,3-dioxane, 1,3-dioxolanes, 4-bromomethyl-1,3-dioxolane, 4-(3-butenyl)-1,3-dioxolane, 4-phenyl-1,3-dioxolane, 4-(2-nitrophenyl)-1,3-dioxolane, 4,5-dimethoxymethyl-1,3-dioxolane, O,O'-phenylenedioxy, and 1,5-dihydro-3H-2,4-benzodioxepin.

Acyclic Dithio Acetals and Ketals

Examples of acyclic dithio acetals and ketals include S,S'-dimethyl, S,S'-diethyl, S,S'-dipropyl, S,S'-dibutyl, S,S'-dipentyl, S,S'-diphenyl, S,S'-dibenzyl, and S,S'-diacetyl.

Cyclic Dithio Acetals and Ketals

Examples of cyclic dithio acetals and ketals include 1,3-dithiane, 1,3-dithiolane, and 1,5-dihydro-3H-2,4-benzodithiepin.

Acyclic Monothio Acetals and Ketals

Examples of acyclic monothio acetals and ketals include O-trimethylsilyl-S-alkyl, O-methyl-S-alkyl or —S-phenyl, and O-methyl-S-2-(methylthio)ethyl.

Cyclic Monothio Acetals and Ketals

Examples of cyclic monothio acetals and ketals include 1,3-oxathiolanes.

Miscellaneous Derivatives

O-Substituted Cyanohydrins

Examples of O-substituted cyanohydrins include O-acetyl, O-trimethylsilyl, O-1-ethoxyethyl, and O-tetrahydropyranyl.

Substituted Hydrazones

Examples of substituted hydrazones include N,N-dimethyl, and 2,4-dinitrophenyl.

Oxime Derivatives

Examples of oxime derivatives include O-methyl, O-benzyl, and O-phenylthiomethyl.

Imines

Substituted Methylene Derivatives, Cyclic Derivatives

Examples of substituted methylene and cyclic derivatives include oxazolidines, 1-methyl-2-(1'-hydroxyalkyl)imidazoles, N,N'-dimethylimidazolidines, 2,3-dihydro-1,3-benzothiazoles, diethylamine adducts, and methylaluminum bis(2,6-di-t-butyl-4-methylphenoxide)(MAD)complex.

Protection for the Carboxyl Group

Esters

Substituted Methyl Esters

Examples of substituted methyl esters include 9-fluorenylmethyl, methoxymethyl, methylthiomethyl, tetrahydropyranyl, tetrahydrofuranyl, methoxyethoxymethyl, 2-(trimethylsilyl)ethoxymethyl, benzyloxymethyl, phenacyl, p-bromophenacyl, α-methylphenacyl, p-methoxyphenacyl, carboxamidomethyl, and N-phthalimidomethyl.

2-Substituted Ethyl Esters

Examples of 2-substituted ethyl esters include 2,2,2-trichloroethyl, 2-haloethyl, ω-chloroalkyl, 2-(trimethylsilyl)ethyl, 2-methylthioethyl, 1,3-dithianyl-2-methyl, 2-(p-nitrophenylsulfenyl)ethyl, 2-(p-toluenesulfonyl)ethyl, 2-(2'-pyridyl)ethyl, 2-(diphenylphosphino)ethyl, 1-methyl-1-phenylethyl, t-butyl, cyclopentyl, cyclohexyl, allyl, 3-buten-1-yl, 4-(trimethylsilyl)-2-buten-1-yl, cinnamyl, α-methylcinnamyl, phenyl, p-(methylmercapto)phenyl, and benzyl.

Substituted Benzyl Esters

Examples of substituted benzyl esters include triphenylmethyl, diphenylmethyl, bis(o-nitrophenyl)methyl, 9-anthrylmethyl, 2-(9,10-dioxo)anthrylmethyl, 5-dibenzosuberyl, 1-pyrenylmethyl, 2-(trifluoromethyl)-6-chromylmethyl, 2,4,6-trimethylbenzyl, p-bromobenzyl, o-nitrobenzyl, p-nitrobenzyl, p-methoxybenzyl, 2,6-dimethoxybenzyl, 4-(methylsulfinyl)benzyl, 4-sulfobenzyl, piperonyl, 4-picolyl, and p-P-benzyl.

Silyl Esters

Examples of silyl esters include trimethylsilyl, triethylsilyl, t-butyldimethylsilyl, i-propyldimethylsilyl, phenyldimethylsilyl, and di-t-butylmethylsilyl.

Activated Esters

Examples of activated esters include thiols.

Miscellaneous Derivatives

Examples of miscellaneous derivatives include oxazoles, 2-alkyl-1,3-oxazolines, 4-alkyl-5-oxo-1,3-oxazolidines, 5-alkyl-4-oxo-1,3-dioxolanes, ortho esters, phenyl group, and pentaminocobalt(III) complex.

Stannyl Esters

Examples of stannyl esters include triethylstannyl and tri-n-butylstannyl.

Amides and Hydrazides

Amides

Examples of amides include N,N-dimethyl, pyrrolidinyl, piperidinyl, 5,6-dihydrophenanthridinyl, o-nitroanilides, N-7-nitroindolyl, N-8-Nitro-1,2,3,4-tetrahydroquinolyl, and p-P-benzenesulfonamides.

Hydrazides

Examples of hydrazides include N-phenyl and N,N'-diisopropyl hydrazides.

C. Synthesis

The compounds of the present invention may be prepared by conventional synthetic organic chemistry and by matrix or combinatorial methods according to Schemes 1 through 6 and Examples 1 through 46 below. Those of ordinary skill in the art will be able to modify and adapt the guidance provided herein to make the disclosed compounds.

The invention provides methods of making the disclosed compounds according to traditional organic synthetic methods as well as parallel, matrix, or combinatorial synthetic methods. Schemes 1 through 6 describe suggested synthetic routes. Using these Schemes, the guidelines below including the I. C. Nordin and J. A. Thomas reference (*Tetrahedron Letters*, 1984, 25(50):5723–5724) and the examples in section E, a person of ordinary skill in the art may develop analogous or similar methods for a given compound.

Examples of the described synthetic routes include synthetic Examples 1 through 46. Compounds analogous to the target compounds of these examples can be, and in may cases have been, made according to analogous routes. The disclosed compounds are useful in basic research, in drug screens, in diagnostic assays, and as pharmaceutical agents.

SCHEME 1

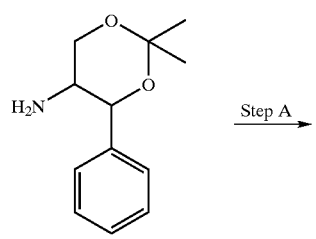

1

Compounds of formula 1 are prepared according to I. C. Nordin and J. A. Thomas (*Tetrahedron Letters*, 1984, 25(50):5723–5724). Compounds of formula 2, where W is O or S, are prepared according to Scheme 1 by reacting amine 1 with a commercially available isocyanate or isothiocyanate. Specifically, amine 1 is dissolved in a solvent such as pentane, toluene, dichloromethane or the like and treated with an isocyanate (or isothiocyanate) directly or a solution of isocyanate (or isothiocyanate) in a solvent such as pentane, toluene, dichloromethane or the like at room temperature. However, the reaction is typically exothermic, and caution should be used. The Nordin reference describes how to make (4S,5S)-2,2-dimethyl-4-phenyl-1,3-dioxan-5-amine (1) from (1S,2S)-2-amino-1-phenyl-1,3-propanediol. In most Examples in this application, "amine 1" is the (4S,5S) stereoisomer. Example 18, where the product is a (4R,5S) urea, is the lone exception. (Some of the other Examples describe the (4S,5S) final product synthesized by a route that does not use amine 1.)

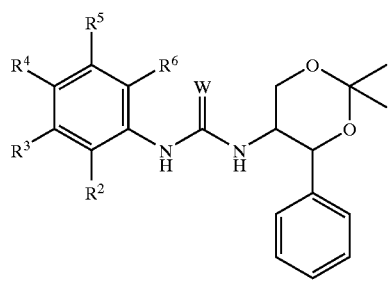

2

SCHEME 2

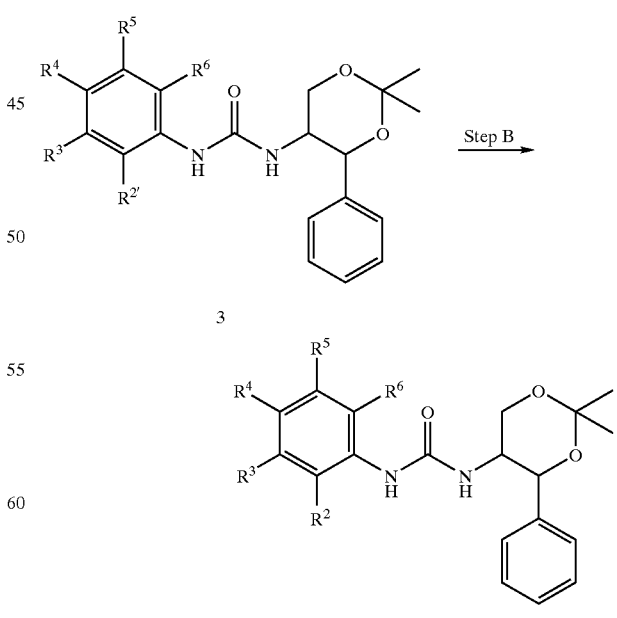

3

2a

Compounds of formula 3, where $R^{2'}$ is I or Br, are prepared according to Scheme 1. Compounds of formula 2a are prepared according to scheme 2 via standard organometallic coupling reactions such as the Suzuki reaction. Relevant references include N. Miyaura and A. Suzuki (*Chem. Rev.* 1995, 95, 2457) and B. I. Alo et al. (*J. Org. Chem.*, 1991, 56, 3763). Specifically, a compound of formula 3 is reacted in Step B with a palladium(0) source such as tetrakis(triphenylphosphine)palladium(0) in a solvent such as ethylene glycol dimethyl ether. Subsequent addition of the desired boronic acid coupling partner dissolved in a solvent such as ethanol or ethylene glycol dimethyl ether and addition of an aqueous solution of sodium carbonate gives a compound of formula 2a via a Suzuki coupling reaction. Suzuki reactions are typically carried out at elevated temperatures, such as 80° C. or the boiling point of the solvent. Various heterocyclic boronic acids such as thiophene boronic acids and pyridine boronic acids may be used in addition to aryl and aryl substituted boronic acids. The Suzuki coupling reaction may also be used to place substituents at positions other than $R^2$, such as at the para position, $R^4$, if desired, assuming the starting material chosen for formula 3 possessed a halogen substituent at the para position. Substitution at $R^2$ in Scheme 2 is shown only as one possible example.

Step B can also represent other reactions of a compound of formula 3 and a palladium(0) source such as tetrakis(triphenyl)phosphine palladium(0) in a solvent such as N,N-dimethylacetamide. For example, reaction with zinc cyanide at elevated temperatures such as 80° C. gives a compound of formula 2a where $R^2$ is a cyano group.

SCHEME 3

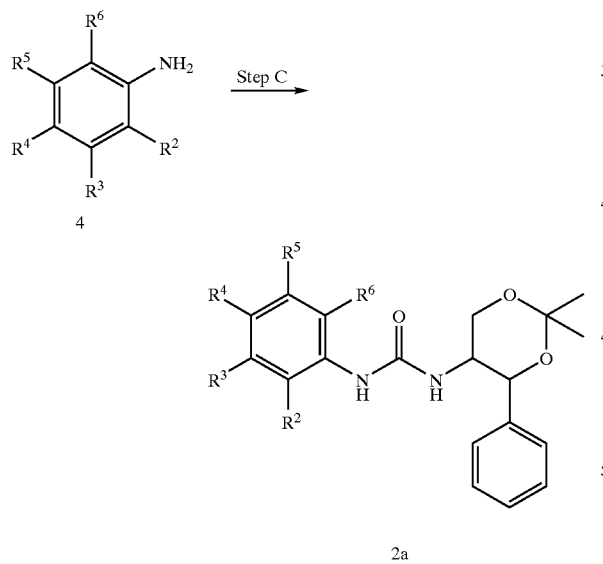

Compounds of formula 2a are prepared according to Scheme 3 by reacting a commercially available aniline of formula 4 with a coupling reagent such as 1,1'-carbonyldiimidazole and amine 1 in Step C. Specifically, a solution of aniline 4 in a solvent such as N,N-dimethylformamide, N,N-dimethylacetamide, dichloromethane or the like is reacted with a coupling reagent such as 1,1'-carbonyldiimidazole or 1,1'-carbonyldiimidazole in the presence of a catalytic amount of 4-(dimethylamino)pyridine. Subsequent addition of amine 1 in a solvent such as N,N-dimethylformamide followed by possible heating to elevated temperatures such as 100° C. or the boiling point of the solvent gives a compound of formula 2a.

SCHEME 4

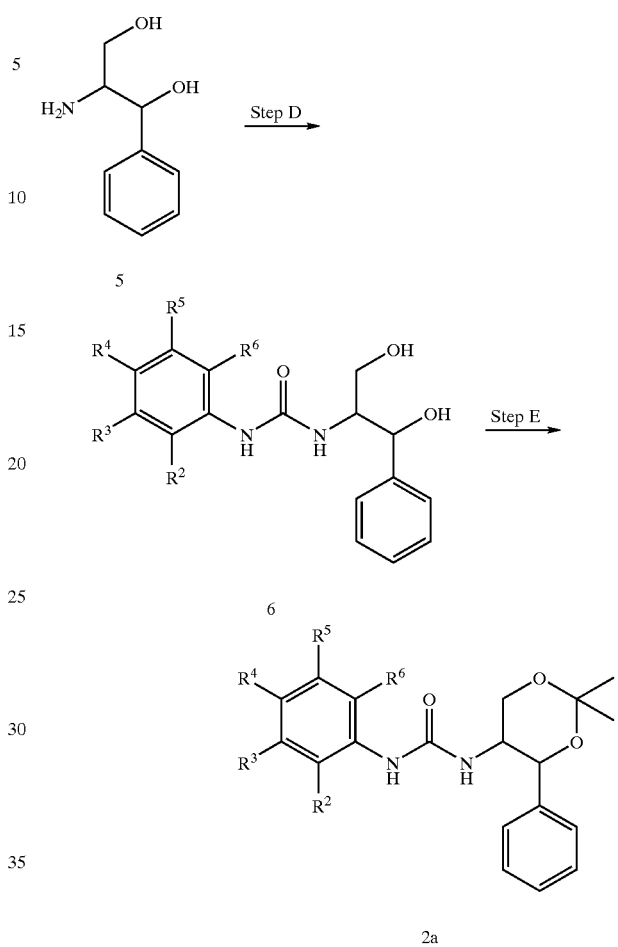

Compounds of formula 6 and formula 2a can be prepared according to Scheme 4. Scheme 4 represents an alternative way of making compounds of formula 2a. Specifically in Step D, a commercially available compound of formula 5 is reacted with a commercially available isocyanate in a solvent such as dichloromethane, N,N-dimethylformamide or the like. A catalytic amount of PS-DMAP may be used in some examples to assist the reaction. In Step E, a compound of formula 6 is exposed to standard acetonide forming conditions such as acetone, 2,2-dimethoxypropane, catalytic p-toluenesulfonic acid in a co-solvent such as N,N-dimethylformamide. Polymer-bound acids such as MP-TsOH may be used and reactions are typically performed at room temperature.

SCHEME 5

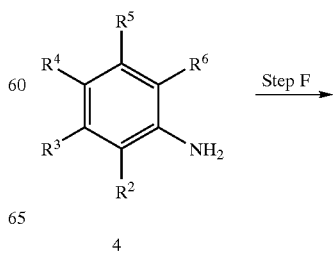

19

-continued

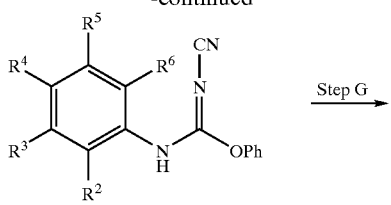

7

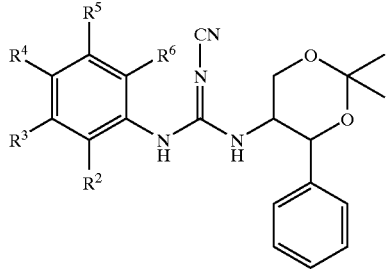

8

Compounds of formula 7 and formula 8 can be prepared according to Scheme 5. Specifically, a commercially available aniline of formula 4 is reacted with commercially available diphenylcyanocarboimidate in a solvent such as acetonitrile at elevated temperature such as the boiling point of the solvent in Step F. A compound of formula 7 is reacted in Step G with amine 1 in a solvent such as acetonitrile at elevated temperature, such as 60° C., to yield cyanoguanidine 8.

SCHEME 6

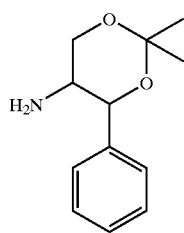

1

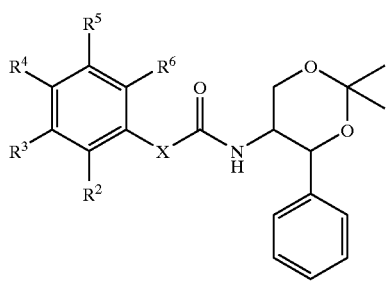

9

Compounds of formula 9, where X is O or $CH_2$, are prepared according to Scheme 6. Specifically, a solution of amine 1 in a solvent such as dichloromethane, 1,2-dichloroethane, N,N-dimethylformamide or the like in the presence of a base such as triethylamine, pyridine, or the like is reacted with a commercially available acid chloride or chloroformate. The reactions are typically exothermic, and caution should be used. Reactions with phenyl acetyl chloride derivatives give amide compounds of formula 9. Reactions with phenyl chloroformate derivatives give carbonate compounds of formula 9.

D. Formulation and Administration

The present compounds inhibit the activity of the orexin-2 receptor and therefore are useful as a medicine especially in methods for treating patients suffering from disorders or conditions that are modulated or regulated by the orexin-2 receptor.

The invention features a method for treating a subject with a condition mediated by orexin-2 receptor, said method comprising administering to the subject a therapeutically effective amount of a pharmaceutical composition comprising a compound of the invention. The invention also provides a method for inhibiting orexin-2 receptor activity in a subject, wherein the method comprises administering to the subject a therapeutically effective amount of a pharmaceutical composition comprising a compound of the invention.

The compounds of the present invention may be formulated into various pharmaceutical forms for administration purposes. To prepare these pharmaceutical compositions, an effective amount of a particular compound, in base or acid addition salt form, as the active ingredient is intimately mixed with a pharmaceutically acceptable carrier.

A carrier may take a wide variety of forms depending on the form of preparation desired for administration. These pharmaceutical compositions are desirably in unitary dosage form suitable, preferably, for oral administration or parenteral injection. For example, in preparing the compositions in oral dosage form, any of the usual pharmaceutical media may be employed. These include water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. In view of their ease in administration, tablets and capsules represent the most advantageous oral dosage unit form, in which case solid pharmaceutical carriers are generally employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Such additives may facilitate the administration to the skin and/or may be helpful for preparing the desired compositions. These compositions may be administered in various ways, e.g., as a transdermal patch, as a spot-on, as an ointment. Acid addition salts of the compounds of formula (I), due to their increased water solubility over the corresponding base form, are more suitable in the preparation of aqueous compositions.

It is especially advantageous to formulate the aforementioned pharmaceutical compositions in dosage unit form for ease of administration and uniformity of dosage. Dosage unit form as used in the specification herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

Pharmaceutically acceptable acid addition salts include the therapeutically active, non-toxic, acid addition salt forms that the disclosed compounds are able to form. The latter can conveniently be obtained by treating the base form with an appropriate acid. Appropriate acids comprise, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic, maleic, fumaric, malic, tartaric, citric, methanesulfonic, ethanesulfonic, benzenesulfonic, p-toluenesulfonic, cyclamic, salicylic, p-aminosalicylic, palmoic and the like acids. The term addition salt also comprises the solvates that the disclosed compounds, as well as the salts thereof, are able to form. Such solvates are for example hydrates, alcoholates and the like. Conversely the salt form can be converted by treatment with alkali into the free base form.

Stereoisomeric forms defines all the possible isomeric forms that the compounds of formula (I) may possess. Unless otherwise mentioned or indicated, the chemical designation of compounds denotes the mixture of all possible stereochemically isomeric forms, said mixtures containing all diastereomers and enantiomers of the basic molecular structure. More in particular, stereogenic centers may have the (R)- or (S)-configuration; substituents on bivalent cyclic saturated radicals may have either the cis- or trans-configuration. The invention encompasses stereochemically isomeric forms including diastereoisomers, as well as mixtures thereof in any proportion of the disclosed compounds. The disclosed compounds may also exist in their tautomeric forms. Such forms although not explicitly indicated in the above and following formulae are intended to be included within the scope of the present invention.

Those of skill in the treatment of disorders or conditions mediated by the orexin-2 receptor could easily determine the effective daily amount from the test results presented hereinafter and other information. In general it is contemplated that a therapeutically effective dose would be from 0.001 mg/kg to 10 mg/kg body weight, more preferably from 0.01 mg/kg to 10 mg/kg body weight. It may be appropriate to administer the therapeutically effective dose as two, three, four or more sub-doses at appropriate intervals throughout the day. Said sub-doses may be formulated as unit dosage forms, for example, containing 0.05 mg to 250 mg, and in particular 0.5 to 50 mg of active ingredient per unit dosage form. Examples include 2 mg, 4 mg, 7 mg, 10 mg, 15 mg, 25 mg, and 35 mg dosage forms. Compounds of the invention may also be prepared in time-release or subcutaneous or transdermal patch formulations. Disclosed compound may also be formulated as a spray or other topical or inhalable formulations.

The exact dosage and frequency of administration depends on the particular compound of formula (I) used, the formulation, the particular condition being treated, the severity of the condition being treated, the age, weight and general physical condition of the particular patient as well as other medication the patient may be taking, as is well known to those skilled in the art. Furthermore, it is evident that said effective daily amount may be lowered or increased depending on the response of the treated patient and/or depending on the evaluation of the physician prescribing the compounds of the instant invention. The effective daily amount ranges mentioned herein are therefore only guidelines.

The next section includes detailed information relating to the preparation, characterization, and use of the disclosed compounds.

E. EXAMPLES

The format of the NMR data is: chemical shift in ppm downfield from the standard (multiplicity, coupling constant J in Hz, integration).

Example 1

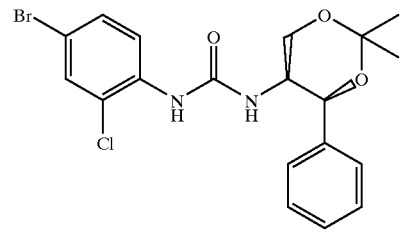

1-(4-Bromo-2-chloro-phenyl)-3-((4S,5S)-2,2-dimethyl-4-phenyl-[1,3]dioxan-5-yl)-urea, $K_i$=9 nM To a stirred or shaken solution of 157 mg (0.76 mmol) of (4S,5S)-2,2-dimethyl-4-phenyl-1,3-dioxan-5-amine (abbreviated as (4S,5S)-amine 1) in pentane (3.5 mL) was added dropwise a solution of 169 mg (0.73 mmol) of 4-bromo-2-chlorophenyl isocyanate in dichloromethane (0.7 mL). A white precipitate was observed after stirring for 0.5 to 2 h. The precipitate was collected, rinsed with pentane, and dried under vacuum to yield 280 mg (88%) of the title compound. In some examples, pentane was used to dissolve the required isocyanate rather than dichloromethane. In addition, if the required isocyanate was a liquid, it was added dropwise as a neat liquid on small-scale reactions such as this. In cases where a precipitate was not observed or the precipitate was not of sufficient purity, the solvent was evaporated, and the residue was purified by column chromatography (hexanes/ethyl acetate) to yield the desired product.

$^1$H NMR (400 MHz, CD$_3$OD): 7.67 (d, J=9.0 Hz, 1H), 7.46 (d, J=2.0 Hz, 1H), 7.40 (m, 2H), 7.26 (m, 4H), 5.30 (d, J=2.0 Hz, 1H), 4.39 (dd, J=12.0 Hz, J=2.0 Hz, 1H), 4.02 (m, 1H), 3.82 (dd, J=12.0 Hz, J=2.0 Hz, 1H), 1.62 (s, 3H), 1.58 (s, 3H).

Example 2

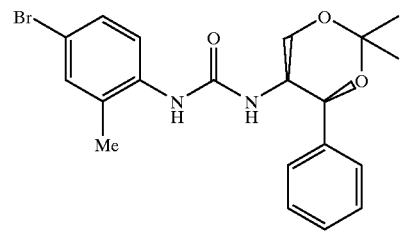

1-(4-Bromo-2-methyl-phenyl)-3-((4S,5S)-2,2-dimethyl-4-phenyl-[1,3]dioxan-5-yl)-urea, $K_i$=50 nM The title compound was prepared according to the general procedure in Example 1 using 4-bromo-2-methylphenyl isocyanate in place of 4-bromo-2-chlorophenyl isocyanate.

¹H NMR (400 MHz, CD₃OD): 7.40 (m, 2H), 7.31 (m, 2H), 7.24 (m, 3H), 7.18 (m, 1H), 6.77 (br d, J=9.5 Hz, 1H), 5.32 (d, J=2.0 Hz, 1H), 4.40 (dd, J=12.0 Hz, 2.0 Hz, 1H), 4.03 (m, 1H), 3.81 (dd, J=12.0 Hz, J=2.0 Hz, 1H), 2.07 (s, 3H), 1.63 (s, 3H), 1.57 (s, 3H).

Example 3

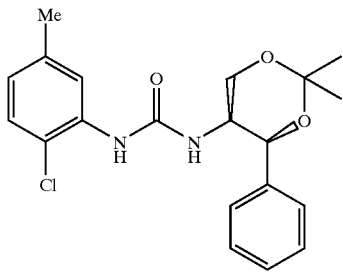

1-(2-Chloro-5-methyl-phenyl)-3-((4S,5S)-2,2-dimethyl-4-phenyl-[1,3]dioxan-5-yl)-urea, K$_i$=27 nM The title compound was prepared according to the general procedure in Example 1 using 2-chloro-5-methylphenyl isocyanate in place of 4-bromo-2-chlorophenyl isocyanate.

¹H NMR (400 MHz, CD₃OD): 7.37 (m, 1H), 7.29 (m, 2H), 7.18 (m, 2H), 7.11 (m, 1H), 7.04 (m, 1H), 6.64 (m, 1H), 5.20 (d, J=1.5 Hz, 1H), 4.29 (dd, J=12.0 Hz, J=2.0 Hz, 1H), 3.91 (m, 1H), 3.70 (dd, J=12.0 Hz, J=2.0 Hz, 1H), 2.12 (s, 3H), 1.51 (s, 3H), 1.46 (s, 3H).

Example 4

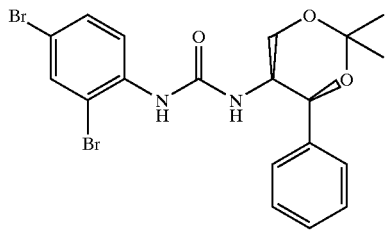

1-(2,4-Dibromo-phenyl)-3-((4S,5S)-2,2-dimethyl-4-phenyl-[1,3]dioxan-5-yl)-urea, K$_i$=10 nM The title compound was prepared according to the general procedure in Example 1 using 2,4-dibromophenyl isocyanate in place of 4-bromo-2-chlorophenyl isocyanate.

¹H NMR (400 MHz, CD₃OD): 7.42 (d, J=2.5 Hz, 1H), 7.29 (d, J=9.0 Hz, 1H), 7.16 (m, 2H), 7.07 (m, 3H), 7.00 (m, 1H), 5.08 (d, J=2.0 Hz, 1H), 4.18 (dd, J=12.0 Hz, J=2.0 Hz, 1H), 3.78 (m, 1H), 3.58 (dd, J=12.0 Hz, J=2.0 Hz, 1H), 1.39 (s, 3H), 1.35 (s, 3H).

Example 5

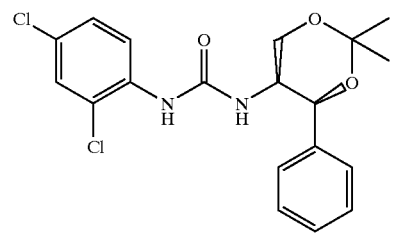

1-(2,4-Dichloro-phenyl)-3-((4S,5S)-2,2-dimethyl-4-phenyl-[1,3]dioxan-5-yl)-urea, K$_i$=15 nM To a solution of 102 mg (0.49 mmol) of (4S,5S)-amine 1 in pentane (3 mL) was added a solution of 74 mg (0.39 mmol) of 2,4-dichlorophenyl isocyanate in dichloromethane (0.1 mL). A white precipitate was observed and collected via filtration. The crude solid was dissolved in dichloromethane (~4 mL) and washed with 0.1 N HCl (~4 mL). The organic layer was washed with brine, dried over magnesium sulfate, filtered, and evaporated to yield 91 mg (59%) of the title compound.

¹H NMR (400 MHz, CD₃OD): 7.59 (d, J=9.0 Hz, 1H), 7.30–7.17(m, 5H), 7.12 (m, 1H), 7.02 (dd, J=9.0 Hz, J=2.5 Hz, 1H), 5.20 (d, 1.5 Hz, 1H), 4.29 (dd, J=12.0 Hz, J=2.0 Hz, 1H), 3.90 (m, 1H), 3.70 (dd, J=12.0 Hz, J=2.0 Hz, 1H), 1.51 (s, 3H), 1.46 (s, 3H).

Example 6

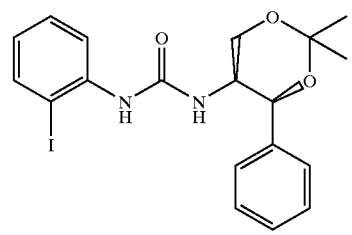

1-((4S,5S)-2,2-Dimethyl-4-phenyl-[1,3]dioxan-5-yl)-3-(2-iodo-phenyl)-urea, K$_i$=70 nM The title compound was prepared according to the general procedure in Example 1 using 2-iodophenyl isocyanate in place of 4-bromo-2-chlorophenyl isocyanate.

¹H NMR (400 MHz, CD₃OD): 7.52 (dd, J=8.0 Hz, J=1.5 Hz, 1H), 7.18 (m, 2H), 7.04 (m, 5H), 6.55 (m, 1H), 5.08 (s, 1H), 4.18 (dd, J=12.0 Hz, J=2.0 Hz, 1H), 3.78 (m, 1H), 3.60 (dd, J=12.0 Hz, J=2.0 Hz, 1H), 1.40 (s, 3H), 1.35 (s, 3H).

Example 7

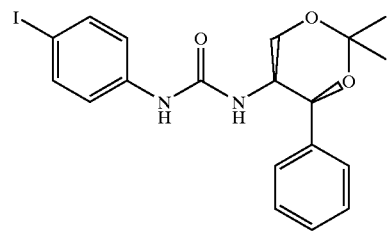

1-((4S,5S)-2,2-Dimethyl-4-phenyl-[1,3]dioxan-5-yl)-3-(4-iodo-phenyl)-urea, $K_i$=45 nM The title compound was prepared according to the general procedure in Example 1 using 4-iodophenyl isocyanate in place of 4-bromo-2-chlorophenyl isocyanate.

$^1$H NMR (400 MHz, CD$_3$OD): 7.36 (m, 2H), 7.27 (m, 2H), 7.19 (m, 2H), 7.10 (m, 1H), 6.90 (m, 2H), 6.30 (br d, J=9.0 Hz, 1H), 5.21 (d, J=1.5 Hz, 1H), 4.26 (dd, J=12.0 Hz, 2.0 Hz, 1H), 3.87 (m, 1H), 3.69 (dd, J=12.0 Hz, 2.0 Hz, 1H), 1.51 (s, 3H), 1.45 (s, 3H).

Example 8

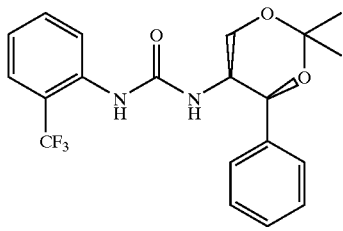

1-((4S,5S)-2,2-Dimethyl-4-phenyl-[1,3]dioxan-5-yl)-3-(2-trifluoromethyl-phenyl)-urea, $K_i$=76 nM The title compound was prepared according to the general procedure in Example 1 using α,α,α-trifluoro-o-tolyl isocyanate in place of 4-bromo-2-chlorophenyl isocyanate.

$^1$H NMR (400 MHz, CD$_3$OD): 7.43 (m, 1H), 7.33–7.04 (m, 8H), 5.20 (br s, 1H), 4.31 (dd, J=12.0 Hz, 2.0 Hz, 1H), 3.91 (m, 1H), 3.70 (dd, J=12.0 Hz, 2.0 Hz, 1H), 1.51 (s, 3H), 1.46 (s, 3H).

Example 9

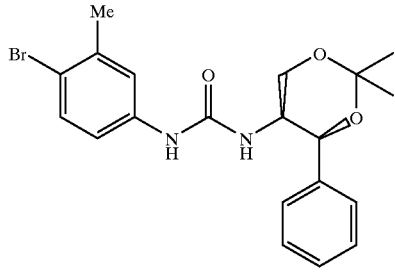

1-(4-Bromo-3-methyl-phenyl)-3-((4S,5S)-2,2-dimethyl-4-phenyl-[1,3]dioxan-5-yl)-urea, $K_i$=87 nM The title compound was prepared according to the general procedure in Example 1 using 4-bromo-3-methylphenyl isocyanate in place of 4-bromo-2-chlorophenyl isocyanate.

$^1$H NMR (400 MHz, CD$_3$OD): 7.28 (m, 2H), 7.18 (m, 3H), 7.11 (m, 1H), 7.02 (m, 1H), 6.82 (m, 1H), 6.29 (brd, J=9.0 Hz, 1H), 5.21 (d, J=1.5 Hz, 1H), 4.27 (dd, J=12.0 Hz, J=2.0 Hz, 1H), 3.88 (m, 1H), 3.69 (dd, J=12.0 Hz, J=2.0 Hz, 1H), 2.17 (s, 3H), 1.51 (s, 3H), 1.45 (s, 3H).

Example 10

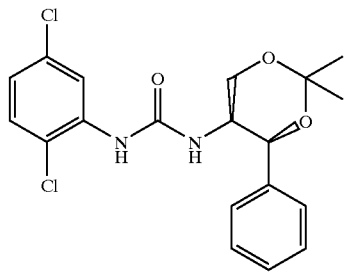

1-(2,5-Dichloro-phenyl)-3-((4S,5S)-2,2-dimethyl-4-phenyl-[1,3]dioxan-5-yl)-urea, $K_i$=98 nM The title compound was prepared according to the general procedure in Example 1 using 2,5-dichlorophenyl isocyanate in place of 4-bromo-2-chlorophenyl isocyanate.

$^1$H NMR (400 MHz, CD$_3$OD): 7.73 (d, J=2.5 Hz, 1H), 7.29 (d, J=7.5 Hz, 2H), 7.15 (m, 4H), 6.80 (dd, J=8.5 Hz, J=2.5 Hz, 1H), 5.21 (s, 1H), 4.30 (dd, J=12.0 Hz, J=2.0 Hz, 1H), 3.91 (m, 1H), 3.70 (dd, J=12.0 Hz, 2.0 Hz, 1H), 1.51 (s, 3H), 1.47 (s, 3H).

Example 11

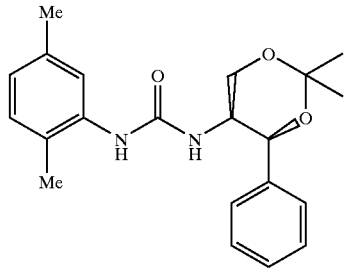

1-(2,5-Dimethyl-phenyl)-3-((4S,5S)-2,2-dimethyl-4-phenyl-[1,3]dioxan-5-yl)-urea, $K_i$=64 nM The title compound was prepared according to the general procedure in Example 1 using 2,5-dimethylphenyl isocyanate in place of 4-bromo-2-chlorophenyl isocyanate.

$^1$H NMR (400 MHz, CD$_3$OD): 7.39–7.33 (m, 2H), 7.33–7.27 (m, 2H), 7.26–7.20 (m, 1H), 7.04–7.01 (br s, 1H), 6.97 (d, J=7.6 Hz, 1H), 6.78 (d, J=7.6 Hz), 6.57–6.49 (m, 1H), 5.30 (br s, 1H), 4.37 (dd, J=12.1 Hz, J=2.0 Hz, 1H), 4.03–3.98 (m, 1H), 3.81 (dd, J=12.1 Hz, J=2.0 Hz, 1H), 2.22 (s, 3H), 2.01 (s, 3H), 1.60 (s, 3H), 1.52 (s, 3H).

Example 12

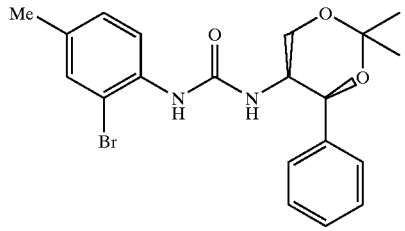

1-(2-Bromo-4-methyl-phenyl)-3-((4S,5S)-2,2-dimethyl-4-phenyl-[1,3]dioxan-5-yl)-urea, K$_i$=5 nM To a stirred solution of 285 mg (1.76 mmol) of 1,1'-carbonyldiimidazole and 5 mg (0.041 mmol) of 4-(dimethylamino)pyridine in N,N-dimethylformamide (3.0 mL) was added 0.22 mL (1.76 mmol) of 2-bromo-4-methylaniline. After stirring for 15 min at 25° C., the reaction was heated to 50° C. At 50° C., a solution of 184 mg (0.88 mmol) of (4S,5S)-amine 1 in N,N-dimethylformamide (1 mL) was added dropwise. The reaction was heated to 100° C. for 4 h and then cooled to 25° C. and partially concentrated under reduced pressure. The mixture was taken up in approximately 100 mL of dichloromethane and washed with water. The organic layers were concentrated to a cream-colored solid that was purified by column chromatography (dichloromethane/ethyl acetate/hexane) to yield 73 mg (20%) of the title compound as a white foam.

$^1$H NMR (400 MHz, CD$_3$OD): 7.39–7.27 (m, 6H), 7.19 (m, 1H), 6.98 (m, 1H), 5.29 (s, 1H), 4.38 (dd, J=12.0 Hz, J=2.0 Hz, 1H), 3.99 (m, 1H), 3.80 (dd, J=12.0 Hz, J=2.0 Hz, 1H), 2.23 (s, 3H), 1.61 (s, 3H), 1.56 (s, 3H).

Example 13

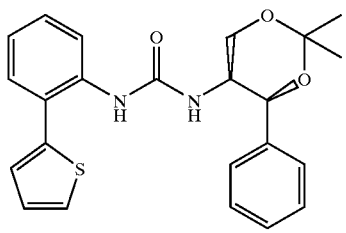

1-((4S,5S)-2,2-Dimethyl-4-phenyl-[1,3]dioxan-5-yl)-3-(2-thiophen-2-yl-phenyl)-urea, K$_i$=34 nM To a reaction flask charged with 10.6 mg (0.0092 mmol) of tetrakis(triphenylphosphine)palladium(0) in ethylene glycol dimethyl ether (1.8 mL) under nitrogen was added 104 mg (0.23 mmol) of the product from Example 6. The resulting yellow solution was stirred for 10–15 min before the addition of 34.5 mg (0.27 mmol) of 2-thiopheneboronic acid dissolved in ethanol (0.2 mL) and ethylene glycol dimethyl ether (0.2 mL) and the subsequent addition of 0.23 mL (0.46 mmol) of a 2 M sodium carbonate aqueous solution. The reaction mixture was heated at 80° C. for 24 h and then cooled to room temperature. The liquid was separated from the solid residue, and the residue was rinsed with dichloromethane, which was subsequently combined with the isolated liquid. The solvent was evaporated, and the crude product was partitioned between brine (~4 mL) and dichloromethane (~4 mL). The organic layer was washed with additional brine, dried over magnesium sulfate, and filtered. The solvent was evaporated, and the dark residue was purified by column chromatography (hexanes/ethyl acetate) to yield 35 mg (37%) of the title compound.

$^1$H NMR (400 MHz, CD$_3$OD): 7.43–7.32 (m, 9H), 7.08 (m, 2H), 6.98 (m, 1H), 6.81 (d, J=9.5 Hz, 1H), 5.31 (d, J=1.5 Hz, 1H), 4.38 (dd, J=12.0 Hz, 2.0 Hz, 1H), 4.06 (m, 1H), 3.81 (dd, J=12.0 Hz, 2.0 Hz, 1H), 1.61 (s, 3H), 1.52 (s, 3H).

Example 14

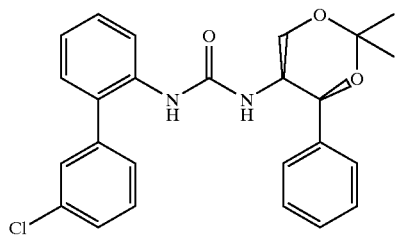

1-(3'-Chloro-biphenyl-2-yl)-3-((4S,5S)-2,2-dimethyl-4-phenyl-[1,3]dioxan-5-yl)-urea, K$_i$=63 nM To a reaction flask charged with 16.2 mg (0.014 mmol) of Tetrakis(triphenylphosphine)palladium(0) in ethylene glycol dimethyl ether (2.0 mL) under nitrogen was added 142 mg (0.31 mmol) of the product from Example 6 and ethylene glycol dimethyl ether (0.8 mL). The resulting yellow solution was stirred for 10 min before the addition of 57.8 mg (0.37 mmol) of 3-chlorophenylboronic acid dissolved in ethylene glycol dimethyl ether (0.6 mL) and the subsequent addition of 0.32 mL (0.65 mmol) of a 2 M sodium carbonate aqueous solution. The reaction mixture was heated at 80° C. for ~24 h and then cooled to room temperature. The liquid was separated from the solid residue, and the residue was rinsed with dichloromethane, which was subsequently combined with the isolated liquid. The solvent was evaporated, and the crude product was partitioned between brine (~4 mL) and dichloromethane (~4 mL). The organic layer was washed with additional brine, dried over magnesium sulfate, and filtered. The solvent was evaporated, and the residue was purified by column chromatography (hexane/ethyl acetate) to yield 80 mg (59%) of the title compound.

$^1$H NMR (400 MHz, CD$_3$OD): 7.25–7.13 (m, 10H), 7.02 (m, 3H), 6.57 (d, J=9.5 Hz, 1H), 5.16 (d, J=2.0 Hz, 1H), 4.23 (dd, J=12.0 Hz, 2.0 Hz, 1H), 3.87 (m, 1H), 3.63 (dd, J=12.0 Hz, 2.0 Hz, 1H), 1.47 (s, 3H), 1.36 (s, 3H).

Example 15

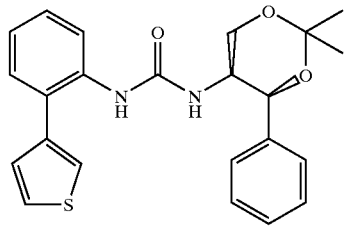

1-((4S,5S)-2,2-Dimethyl-4-phenyl-[1,3]dioxan-5-yl)-3-(2-thiophen-3-yl-phenyl)-urea, K$_i$=100 nM To a reaction flask charged with 14.7 mg (0.013 mmol) of tetrakis(triphenylphosphine)palladium(0) in ethylene glycol dimethyl ether (2.5 mL) under nitrogen was added 125 mg (0.27 mmol) of the product from Example 6. The resulting yellow solution was stirred for 10 min before the addition of 41.0 mg (0.32 mmol) of 3-thiopheneboronic acid dissolved in ethanol (0.2 mL) and the subsequent addition of 0.27 mL (0.54 mmol) of a 2 M sodium carbonate aqueous solution. The reaction mixture was heated at 80° C. for ~20 h and then cooled to room temperature. The liquid was separated from the solid residue, and the residue was rinsed with dichloromethane, which was subsequently combined with the isolated liquid. The solvent was evaporated, and the crude product was partitioned between brine (~4 mL) and dichloromethane (~4 mL). The organic layer was washed with additional brine, dried over magnesium sulfate, and filtered. The solvent was evaporated, and the residue was purified by column chromatography (hexane/ethyl acetate) to yield 55 mg (50%) of the title compound.

$^1$H NMR (400 MHz, CD$_3$OD): 7.33–7.15 (m, 9H), 6.99 (m, 2H), 6.84 (m, 1H), 6.65 (d, J=9.5 Hz, 1H), 5.20 (d, J=2.0 Hz, 1H), 4.27 (dd, J=12.0 Hz, 2.0 Hz, 1H), 3.96 (m, 1H), 3.68 (dd, J=12.0 Hz, 2.0 Hz, 1H), 1.49 (s, 3H), 1.40 (s, 3H).

Example 16

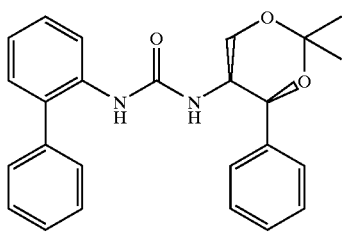

1-Biphenyl-2-yl-3-((4S,5S)-2,2-dimethyl-4-phenyl-[1,3]dioxan-5-yl)-urea, K$_i$=56 nM The title compound was prepared according to the general procedure in Example 1 using 2-biphenylyl isocyanate in place of 4-bromo-2-chlorophenyl isocyanate.

$^1$H NMR (400 MHz, CD$_3$OD): 7.41–7.06 (m, 14H), 6.75–6.69 (m, 1H), 5.28–5.25 (m, 1H), 4.35 (dd, J=12.0 Hz, J=2.0 Hz, 1H), 4.04–3.98 (m, 1H), 3.75 (dd, J=12.0 Hz, J=2.0 Hz, 1H), 1.58 (s, 3H), 1.46 (s, 3H).

Example 17

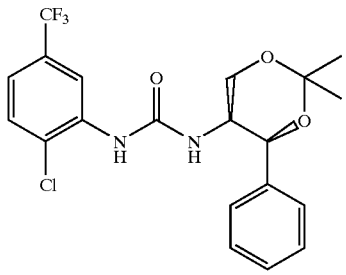

1-(2-Chloro-5-trifluoromethyl-phenyl)-3-((4S,5S)-2,2-dimethyl-4-phenyl-[1,3]dioxan-5-yl)-urea, K$_i$=120 nM The title compound was prepared according to the general procedure in Example 1 using 2-chloro-5-(trifluoromethyl) phenyl isocyanate in place of 4-bromo-2-chlorophenyl isocyanate.

$^1$H NMR (400 MHz, CD$_3$OD): 8.00 (d, J=1.0 Hz, 1H), 7.35 (m, 1H), 7.27 (m, 2H), 7.15 (m, 2H), 7.05 (m, 2H), 5.18 (d, J=2.0 Hz, 1H), 4.27 (dd, J=12.0 Hz, J=2.0 Hz, 1H), 3.88 (m, 1H), 3.67 (dd, J=12.0 Hz, J=2.0 Hz, 1H), 1.48 (s, 3H), 1.44 (s, 3H).

Example 18

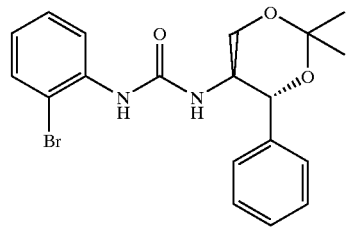

1-(2-Bromo-phenyl)-3-((4R,5S)-2,2-dimethyl-4-phenyl-[1,3]dioxan-5-yl)-urea, K$_i$=130 nM Step A:

A solution of 0.188 g of (1R,2S)-(+)-2-amino-1-phenyl-1,3-propanediol in methanol (6 mL) was treated with 0.083 mL of methyl formate. After stirring overnight at ambient temperature, the mixture was concentrated in vacuo and used without further purification.

Step B:

A solution of the product from Step A (0.218 g) in acetone (5 mL) was treated with 0.207 mL of 2,2-dimethoxypropane and cooled in an ice bath. The mixture was treated with 0.075 mL of a 1.0M HBr in methanol solution. The solution was allowed to warm to room temperature over a 24 h period. The mixture was concentrated in vacuo and used without further purification.

Step C:

To the product from Step B (0.263 g) was added 5 mL of hydrazine hydrate, and the mixture refluxed for 90 min. The solution was diluted with water and extracted with toluene. The combined organic extracts were washed with water, dried over sodium sulfate, filtered and concentrated in vacuo to 0.142 g of a colorless oil.

Step D:

The product from Step C (0.061 mg) was dissolved in 2 mL of toluene and treated with 0.037 mL of 2-bromophenyl isocyanate. After 20 min the mixture was concentrated in vacuo to afford 0.117 g of the title compound.

$^1$H NMR (400 MHz, CD$_3$OD): 7.53 (dd, J=8.0 Hz, J=1.5 Hz, 1H), 7.47 (dd, J=8.0 Hz, J=1.5 Hz, 1H), 7.43–7.37 (m, 2H), 7.35–7.26 (m, 2H), 7.24–7.13 (m, 2H), 6.90–6.84 (m, 1H), 5.30 (br s, 1H), 4.40 (dd, J=12.0 Hz, J=2.0 Hz, 1H), 4.04–3.98 (m, 1H), 3.81 (dd, J=12.0 Hz, J=2.0 Hz, 1H), 1.62 (s, 3H), 1.57 (s, 3H).

Example 19

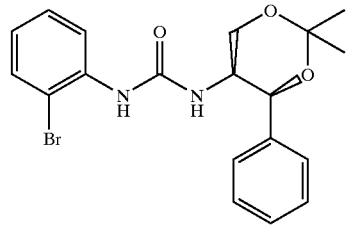

1-(2-Bromo-phenyl)-3-((4S,5S)-2,2-dimethyl-4-phenyl-[1,3]dioxan-5-yl)-urea, K$_i$=97 nM Step A:

A mixture of (1S,2S)-(+)-2-amino-1-phenyl-1,3-propanediol (815 mg, 4.9 mmol), 2-bromophenyl isocyanate (970 mg, 0.6 mL) and solid supported-DMAP (cat. 10 mol %) in dichloromethane (15 mL) and DMF (3 mL) was allowed to stir at room temperature overnight (ca. 15 h). The reaction mixture was washed with water, and the organic layer was separated, dried over anhydrous sodium sulfate, and filtered. The filtrate was concentrated in vacuo, and the crude product was purified on silica gel eluting with 50% ethyl acetate in hexanes to yield 1.35 g (75%) of a white solid.

Step B:

A mixture of the product from Step A (1.35 g, 3.7 mmol), 2,2-dimethoxypropane (5.0 mL), solid supported toluenesulfonic acid (cat. 10 mol %) and acetone (10 mL) in DMF (10 mL) was allowed to stir at room temperature for 8 h. The reaction mixture was concentrated in vacuo, and the crude product was taken up in ethyl acetate (20 mL) and washed with water. The organic layer was separated, dried over anhydrous sodium sulfate, and filtered. The filtrate was concentrated in vacuo, and the residue was purified on silica gel eluting with 15–30% ethyl acetate in hexanes to yield 0.98 g of the title compound as a white solid (65% yield).

$^1$H NMR (400 MHz, CD$_3$OD): 7.52 (dd, 1H, J=1.5 and 8.3 Hz), 7.45 (dd, 1H, J=1.4 and 8.0 Hz), 7.39 (d, 2H, J=7.6 Hz), 7.29 (t, 2H, J=7.5 Hz), 7.19 (m, 2H), 6.85 (dt, 1H, J=1.6 and 7.5 Hz), 5.29 (s, 1H), 4.38 (dd, 1H, J=1.8 and 11.8 Hz), 4.0 (d, 1H, J=1.8 Hz), 3.80 (dd, 1H, J=1.8 and 11.8 Hz), 1.60 (s, 3H), 1.56 (s, 3H).

Example 20

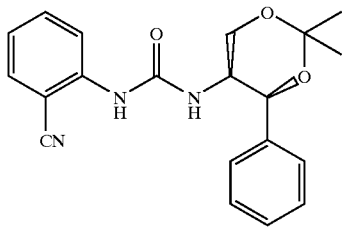

1-(2-Cyano-phenyl)-3-((4S,5S)-2,2-dimethyl-4-phenyl-[1,3]dioxan-5-yl)-urea, K$_i$=60 nM A mixture of the product from Example 19 (355 mg, 0.88 mmol), tetrakis(triphenylphosphine)palladium(0) (102 mg, 10 mol %) and zinc cyanide (103 mg, 0.88 mmol) in dimethylacetamide (8.0 mL) was heated at 80° C. for 8 h. The reaction mixture was cooled to room temperature and diluted with ethyl acetate (25 mL). The organic layer was washed with water, separated, dried over anhydrous sodium sulfate, and filtered. The filtrate was concentrated in vacuo to afford 309 mg of the title compound.

$^1$H NMR (400 MHz, CDCl$_3$): 7.64 (d, 1H, J=8.2 Hz), 7.47 (d, 1H, J=8.0 Hz), 7.35 (m, 4H), 7.23 (m, 1H), 7.26 (m, 2H), 7.19 (t, 1H, J=6.5 Hz), 6.88 (t, 1H, J=6.5 Hz), 6.46 (s, 2H), 5.46 (d, 1H, J=9.1 Hz), 5.24 (s, 1H), 4.31 (dd, 1H, J=1.6 and 12.0 Hz), 4.19 (dd, 1H, J=1.6 and 9.1 Hz), 3.98 (dd, 1H, J=1.6 and 12.0 Hz), 1.61 (s, 3H), 1.57 (s, 3H).

Example 21

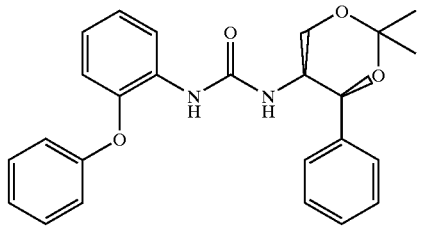

1-((4S,5S)-2,2-Dimethyl-4-phenyl-[1,3]dioxan-5-yl)-3-(2-phenoxy-phenyl)-urea, K$_i$=210 nM The title compound was prepared according to the general procedure in Example 1 using 2-phenoxyphenyl isocyanate in place of 4-bromo-2-chlorophenyl isocyanate.

$^1$H NMR (400 MHz, CD$_3$OD): 7.83 (dd, J=8.34 Hz, J=1.52 Hz, 1H), 7.42–7.06 (m, 8H), 7.02–6.83 (m, 4H), 6.80–6.73 (m, 1H), 5.27 (br s, 1H), 4.36 (dd, J=12.0 Hz, J=2.0 Hz, 1H), 4.01–3.95 (m, 1H), 3.77 (dd, J=12.0 Hz, J=2.0 Hz, 1H), 1.59 (s, 3H), 1.51 (s, 3H).

Example 22

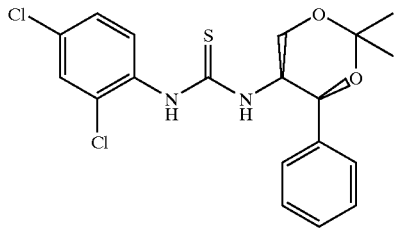

1-(2,4-Dichloro-phenyl)-3-((4S,5S)-2,2-dimethyl-4-phenyl-[1,3]dioxan-5-yl)-thiourea, K$_i$=280 nM To a solution of 130 mg (0.62 mmol) of (4S,5S)-amine 1 in pentane (2.0 mL) was added dropwise a solution of 116 mg (0.62 mmol) of 2,4-dichlorophenyl isothiocyanate in dichloromethane (0.15 mL). After stirring for ~24 h, a white precipitate was collected, rinsed with pentane, and dried under reduced pressure to yield 172 mg (67%) of the title compound.

$^1$H NMR (400 MHz, CD$_3$OD): 7.36 (m, 2H), 7.21 (m, 4H), 7.14 (m, 2H), 5.27 (br s, 1H), 4.73 (br s, 1H), 4.25 (dd, J=12.0 Hz, 2.0 Hz, 1H), 3.90 (dd, J=12.0 Hz, 2.0 Hz, 1H), 1.52 (s, 3H), 1.42 (s, 3H).

Example 23

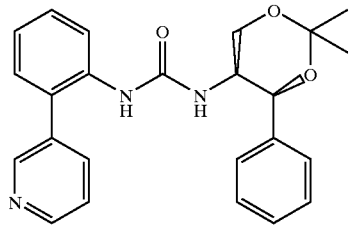

1-((4S,5S)-2,2-Dimethyl-4-phenyl-[1,3]dioxan-5-yl)-3-(2-pyridin-3-yl-phenyl)-urea, K$_i$=320 nM To a reaction flask charged with 10.8 mg (0.0094 mmol) of tetrakis(triphenylphosphine)palladium(0) in ethylene glycol dimethyl ether (1.8 mL) under nitrogen was added 107 mg (0.24 mmol) of the product from Example 6. The resulting yellow solution was stirred for 15 min before the addition of 34.0 mg (0.28 mmol) of pyridine-3-boronic acid dissolved in ethanol (0.4 mL) and ethylene glycol dimethyl ether (0.2 mL), and the subsequent addition of 0.23 mL (0.47 mmol) of a 2 M sodium carbonate aqueous solution. The reaction mixture was heated at 80° C. for ~20 h and then cooled to room temperature. The liquid was separated from the solid residue, and the residue was rinsed with dichloromethane, which was subsequently combined with the isolated liquid. The solvent was evaporated, and the crude product was partitioned between brine (~4 mL) and dichloromethane (~4 mL). The organic layer was washed with additional brine, dried over magnesium sulfate, and filtered. The solvent was evaporated, and the residue, an orange oil, was purified by column chromatography (hexane/ethyl acetate) to yield 35 mg (36%) of the title compound.

$^1$H NMR (400 MHz, CD$_3$OD): 8.36 (m, 2H), 7.49 (m, 1H), 7.33–7.05 (m, 10H), 6.47 (m, 1H), 5.15 (d, J=2.0 Hz, 1H), 4.23 (dd, J=12.0 Hz, 2.0 Hz, 1H), 3.87 (m, 1H), 3.60 (dd, J=12.0 Hz, 2.0 Hz, 1H), 1.44 (s, 3H), 1.36 (s, 3H).

Example 24

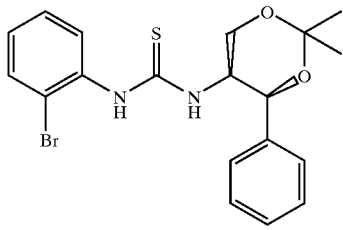

1-(2-Bromo-phenyl)-3-((4S,5S)-2,2-dimethyl-4-phenyl-[1,3]dioxan-5-yl)-thiourea, K$_i$=540 nM To a solution of 143 mg (0.69 mmol) of (4S,5S)-amine 1 in pentane (2.0 mL) was added dropwise 93 microliters (0.69 mmol) of 2-bromophenyl isothiocyanate. After ~48 h, a white precipitate was collected, rinsed with pentane and dried under reduced pressure to yield 155 mg (53%) of the title compound.

$^1$H NMR (400 MHz, CD$_3$OD): 7.50 (d, J=9.0 Hz, 1H), 7.16 (m, 7H), 7.05 (m, 1H), 5.25 (d, J=2.0 Hz, 1H), 4.67 (br s, 1H), 4.23 (dd, J=12.0 Hz, 1.5 Hz, 1H), 3.92 (dd, J=12.0 Hz, 2.0 Hz, 1H), 1.48 (s, 3H), 1.35 (s, 3H).

Example 25

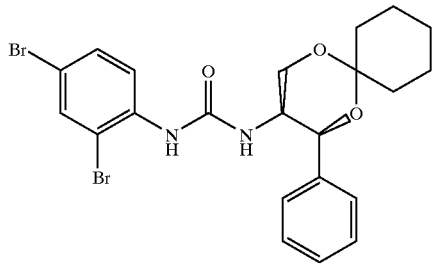

1-(2,4-Dibromo-phenyl)-3-((2S,3S)-2-phenyl-1,5-dioxa-spiro[5.5]undec-3-yl)-urea, K$_i$=700 nM Step A:

A reaction flask was charged with 490 mg (2.5 mmol) of N-((1S,2S)-2-hydroxy-1-hydroxymethyl-2-phenyl-ethyl)-formamide (Nordin, I. C.; Thomas, J. A. Tetrahedron Letters, 1984, 25(50):5723–5724), cyclohexanone (2.0 mL) and 15 mg (0.078 mmol) of p-toluenesulfonic acid monohydrate. The reaction mixture was heated to 100° C. under nitrogen for approximately 8 h then cooled to room temperature. The product was concentrated and then purified by column chromatography to yield 80 mg (12%) of an oil.

Step B:

A flask charged with 70 mg (0.25 mmol) of the product from Step A and hydrazine hydrate (1.0 mL) was heated to 105° C. for 2.5 h. After cooling to room temperature, the reaction mixture was partitioned between toluene (15 mL) and water (15 mL). The aqueous layer was washed with additional toluene, and the combined organic layers were washed with brine, dried over magnesium sulfate, and filtered. The solvent was evaporated to yield 35 mg (57%) of an oil.

Step C:

To a solution of 20 mg (0.081 mmol) of the product from Step B in pentane (0.5 mL) was added dropwise a solution of 22.4 mg (0.081 mmol) of 2,4-dibromophenyl isocyanate in dichloromethane (0.3 mL). After a white solid was observed, the reaction mixture was concentrated, and the residue was purified via column chromatography (hexane/ethyl acetate) to yield 15 mg (35%) of the title compound.

$^1$H NMR (400 MHz, CD$_3$OD): 7.53 (d, J=2.5 Hz, 1H), 7.43 (d, J=9.0 Hz, 1H), 7.31 (m, 2H), 7.19 (m, 3H), 7.11 (m, 1H), 5.21 (br s, 1H), 4.30 (dd, J=12.0 Hz, 2.0 Hz, 1H), 3.95 (m, 1H), 3.67 (dd, J=12.0 Hz, 2.0 Hz, 1H), 2.05–1.39 (m, 10H).

Example 26

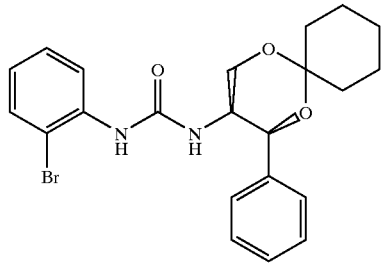

1-(2-Bromo-phenyl)-3-((2S,3S)-2-phenyl-1,5-dioxa-spiro[5.5]undec-3-yl)-urea, K$_i$=980 nM To a solution of 26 mg (0.10 mmol) of the product from Example 25 Step B in pentane (0.7 mL) and dichloromethane (0.3 mL) was added dropwise 12.4 microliters (0.10 mmol) of 2-bromophenyl isocyanate. After stirring overnight, the reaction mixture was concentrated under reduced pressure, and the residue was purified via column chromatography (hexane/ethyl acetate) to yield 26 mg (58%) of the title compound.

$^1$H NMR (400 MHz, CD$_3$OD): 7.44 (m, 1H), 7.34 (m, 3H), 7.21 (m, 2H), 7.09 (m, 2H), 6.77 (m, 1H), 5.21 (brs, 1H), 4.31 (dd, J=12.0 Hz, 2.0 Hz, 1H), 3.95 (m, 1H), 3.69 (dd, J=12.0 Hz, 2.0 Hz, 1H), 2.05–1.39 (m, 10H).

Example 27

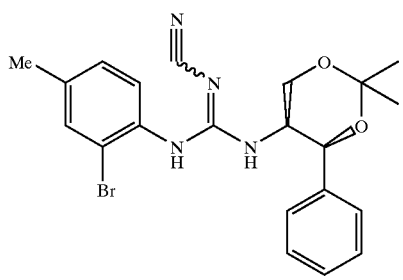

N-(2-Bromo-4-methyl-phenyl)-N'-((4S,5S)-2,2-dimethyl-4-phenyl-[1,3]dioxan-5-yl)-N"-cyanoguanidine, $K_i$=1,000 nM Step A:

To a solution of 212 mg (0.89 mmol) of diphenylcyanocarbonimidate in acetonitrile (4.5 mL) was added 0.11 mL (0.89 mmol) of 2-bromo-4-methylaniline. The resulting solution was heated to 78° C. under nitrogen for 24 h, cooled to room temperature and slowly concentrated. The residue was purified by column chromatography (hexanes/ethyl acetate) to yield 65 mg (22%) of a white solid.

Step B:

A solution of 33 mg (0.10 mmol) of the product from Step A, 31 mg (0.15 mmol) of (4S,5S)-amine 1, and acetonitrile (1.2 mL) was heated to 75° C. for approximately 10 h. The crude mixture was purified by column chromatography (hexane/ethyl acetate) to yield 10 mg (23%) of the title compound.

$^1$H NMR (400 MHz, CD$_3$OD): 7.41 (br s, 1H), 7.17 (m, 6H), 6.83 (m, 1H), 5.19 (s, 1H), 4.22 (m, 1H), 4.00 (m, 1H), 3.77 (m, 1H), 2.26 (s, 3H), 1.46 (s, 3H), 1.27 (s, 3H).

Example 28

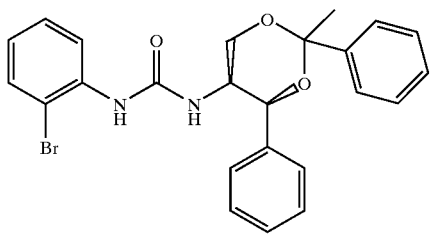

1-(2-Bromo-phenyl)-3-((4S,5S)-2-methyl-2,4-diphenyl-[1,3]dioxan-5-yl)-urea, $K_i$=2,600 nM Step A:

A reaction flask was charged with 860 mg (4.4 mmol) of N-((1S,2S)-2-hydroxy-1-hydroxymethyl-2-phenyl-ethyl)-formamide (Nordin, I. C.; Thomas, J. A. *Tetrahedron Letters*, 1984, 25(50):5723–5724), 1.2 mL (7.5 mmol) of 1,1 dimethoxyethylbenzene, 20 mg (0.10 mmol) of p-toluenesulfonic acid monohydrate in dichloromethane (5.0 mL) and N,N-dimethylformamide (2.0 mL). The reaction mixture was stirred for 4 h at room temperature, then an additional 15 mg of p-toluenesulfonic acid monohydrate was added, and the solution was heated to 60° C. for 19 h. After addition of N,N-dimethylformamide (1 mL), the reaction mixture was heated to 100° C. for 2 h and then cooled to room temperature, and concentrated. The residue was purified by column chromatography (hexanes/ethyl acetate) to yield 720 mg (55%) of a foam.

Step B:

A reaction flask charged with 540 mg (1.8 mmol) of the product from Step A and hydrazine hydrate (2.8 mL) was heated to 100° C. for 3 h. The reaction mixture was cooled to room temperature and partitioned between toluene (15 mL) and water (15 mL). The aqueous layer was extracted with two fresh portions of toluene. The combined organic layers were washed with water, dried over sodium sulfate, filtered and concentrated. The residue was purified by column chromatography (hexane/ethyl acetate) to yield 125 mg (26%) of an oil.

Step C:

To a solution of 45 mg (0.17 mmol) of the product from Step B in dichloromethane (1 mL) and pentane (0.5 mL) was added 20 microliters (0.17 mmol) of 2-bromophenyl isocyanate. After stirring for 24 h at room temperature, the reaction mixture was concentrated, and the residue was purified by column chromatography (hexanes/ethyl acetate) to yield 48 mg (61%) of the title compound.

$^1$H NMR (400 MHz, CD$_3$OD): 7.72 (m, 2H), 7.50 (m, 3H), 7.37 (m, 6H), 7.25 (m, 1H), 7.16 (m, 1H), 6.84 (m, 1H), 5.58 (s, 1H), 4.62 (m, 1H), 4.17 (m, 1H), 3.97 (m, 1H), 1.85 (s, 3H).

Example 29

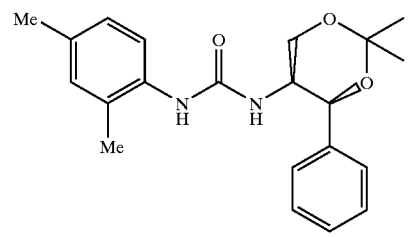

1-(2,4-Dimethyl-phenyl)-3-((4S,5S)-2,2-dimethyl-4-phenyl-[1,3]dioxan-5-yl)-urea, $K_i$=200 nM The title compound was prepared according to the general procedure in Example 1 using 2,4-dimethylphenyl isocyanate in place of 4-bromo-2-chlorophenyl isocyanate.

$^1$H NMR (400 MHz, CD$_3$OD): 7.37–7.26 (m, 4H), 7.25–7.20 (m, 1H), 7.02 (d, 7.83 Hz, 1H), 6.92 (br s, 1H), 6.87 (d, 7.83 Hz, 1H), 6.47–6.38 (m, 1H), 5.29 (br s, 1H), 4.36 (dd, J=12.0 Hz, J=2.0 Hz, 1H), 4.01–3.96 (m, 1H), 3.80 (dd, J=12.0 Hz, J=2.0 Hz, 1H), 2.23 (s, 3H), 2.00 (s, 3H), 1.60 (s, 3H), 1.51 (s, 3H).

Example 30

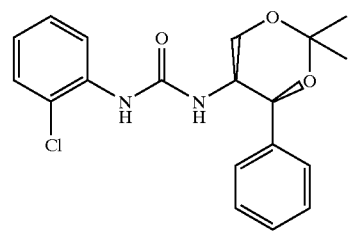

1-(2-Chloro-phenyl)-3-((4S,5S)-2,2-dimethyl-4-phenyl-[1,3]dioxan-5-yl)-urea, $K_i$=300 nM The title compound was prepared according to the general procedure in Example 1 using 2-chlorophenyl isocyanate in place of 4-bromo-2-chlorophenyl isocyanate.

$^1$H NMR (400 MHz, CD$_3$OD): 7.65 (m, 1H), 7.39 (m, 2H), 7.29 (m, 3H), 7.21 (m, 1H), 7.11 (m, 1H), 6.91 (m, 1H), 5.30 (d, J=1.5 Hz, 1H), 4.39 (dd, J=12.0 Hz, 2.0 Hz, 1H), 4.01 (m, 1H), 3.81 (dd, J=12.0 Hz, 2.0 Hz, 1H), 1.61 (s, 3H), 1.56 (s, 3H).

Example 31

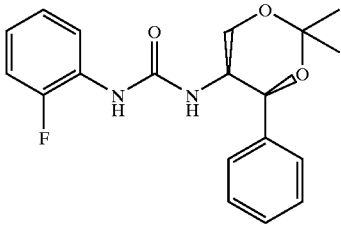

1-((4S,5S)-2,2-Dimethyl-4-phenyl-[1,3]dioxan-5-yl)-3-(2-fluoro-phenyl)-urea, K$_i$=1,550 nM The title compound was prepared according to the general procedure in Example 1 using 2-fluorophenyl isocyanate in place of 4-bromo-2-chlorophenyl isocyanate.

$^1$H NMR (400 MHz, CD$_3$OD): 7.75 (t, J=8.0 Hz, 1H), 7.43–7.35 (m, 2H), 7.29 (t. J=7.3 Hz, 2H), 7.24–7.17 (m, 1H), 7.05–6.85 (m, 4H), 5.31 (br s, 1H), 4.38 (dd. J=12.0 Hz, J=2.0 Hz, 1H), 4.02–3.95 (m, 1H), 3.81 (dd, J=12.0 Hz, J=2.0 Hz, 1H), 1.61 (s, 3H), 1.56 (s, 3H).

Example 32

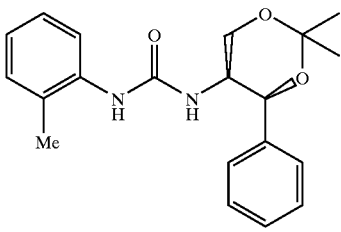

1-((4S,5S)-2,2-Dimethyl-4-phenyl-[1,3]dioxan-5-yl)-3-o-tolyl-urea, K$_i$=650 nM

The title compound was prepared according to the general procedure in Example 1 using o-tolyl isocyanate in place of 4-bromo-2-chlorophenyl isocyanate.

$^1$H NMR (400 MHz, CD$_3$OD): 7.43–7.17 (m, 6H), 7.13–7.01 (m, 2H), 6.98–6.91 (m, 1H), 6.64–6.51 (m, 1H), 5.30 (br s, 1H), 4.38 (dd, J=12.0 Hz, J=2.0 Hz, 1H), 4.04–3.97 (m, 1H), 3.81 (dd, J=12.0 Hz, J=2.0 Hz 1H), 2.06 (s, 3H), 1.60 (s, 3H), 1.53 (s, 3H).

Example 33

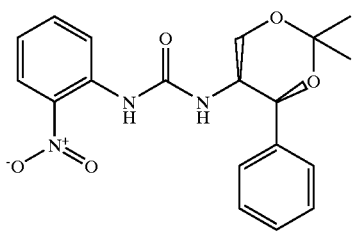

1-((4S,5S)-2,2-Dimethyl-4-phenyl-[1,3]dioxan-5-yl)-3-(2-nitro-phenyl)-urea, K$_i$=580 nM The title compound was prepared according to the general procedure in Example 1 using 2-nitrophenyl isocyanate in place of 4-bromo-2-chlorophenyl isocyanate.

$^1$H NMR (400 MHz, CD$_3$OD): 8.01 (dd, J=8.6 Hz, J=1.8 Hz, 1H), 7.82–7.75 (m, 1H), 7.51–7.45 (m, 1H), 7.42–7.37 (m, 2H), 7.31–7.24 (m, 2H), 7.22–7.16 (m, 1H), 7.10–7.04 (m, 1H), 5.31 (br s, 1H), 4.42 (dd, J=12.0 Hz, J=2.0 Hz, 1H), 4.05–4.00 (m, 1H), 3.81 (dd, J=12.0 Hz, J=2.0 Hz, 1H), 1.62 (s, 3H), 1.58 (s, 3H).

Example 34

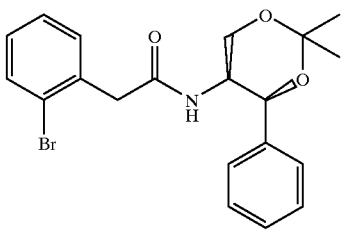

2-(2-Bromo-phenyl)-N-((4S,5S)-2,2-dimethyl-4-phenyl-[1,3]dioxan-5-yl)-acetamide, K$_i$=2,200 nM To a solution of 250 mg (1.2 mmol) of (4S,5S)-amine 1 in dichloromethane (3 mL) was added 0.16 mL (1.2 mmol) of triethylamine followed by dropwise addition of 0.17 mL (1.2 mmol) of 2-bromophenylacetyl chloride. After stirring for ~96 h at 25° C., the reaction mixture was concentrated under reduced pressure, and the residue was purified by column chromatography (hexanes/ethyl acetate) to yield 290 mg (60%) of the title compound.

$^1$H NMR (400 MHz, CDCl$_3$): 7.55 (m, 1H), 7.26 (m, 4H), 7.16 (m, 3H), 7.06 (m, 1H), 6.13 (m, 1H), 5.15 (br s, 1H), 4.19 (m, 2H), 3.90 (, 1H), 3.60 (m, 1H), 3.50 (m, 1H), 1.55 (s, 3H), 1.45 (s, 3H).

Example 35

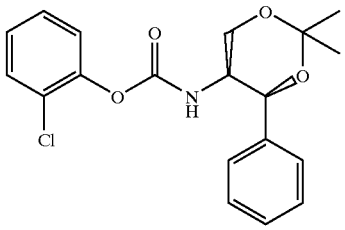

((4S,5S)-2,2-Dimethyl-4-phenyl-[1,3]dioxan-5-yl)-carbamic acid 2-chloro-phenyl ester, $K_i$=2,600 nM To a solution of 218 mg (1.05 mmol) of (4S,5S)-amine 1 in dichloromethane (3 mL) was added 0.15 mL (1.05 mmol) of triethylamine followed by 0.14 mL (1.05 mmol) of 2-chlorophenyl chloroformate. After stirring for ~18 h at 25° C., the reaction mixture was concentrated under reduced pressure, and the residue was purified by column chromatography (hexanes/ethyl acetate) to yield 90 mg (23%) of the title compound in approximately 85% purity.

$^1$H NMR (400 MHz, C$_6$D$_6$): 7.37 (m, 2H), 7.25 (m, 2H), 7.15 (m, 1H), 7.01 (dd, J=8.0 Hz, J=1.5 Hz, 1H), 6.79 (dd, J=8.0 Hz, J=1.5 Hz, 1H), 6.67 (m, 1H), 6.52 (m, 1H), 5.77 (m, 1H), 4.74 (d, J=2.0 Hz, 1H), 3.76 (m, 2H), 3.62 (dd, J=12.0 Hz, J=2.0 Hz, 1H), 1.40 (s, 3H), 1.11 (s, 3H).

Example 36

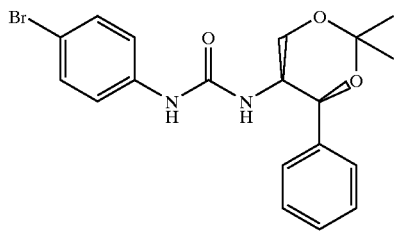

1-(4-Bromo-phenyl)-3-((4S,5S)-2,2-dimethyl-4-phenyl-[1,3]dioxan-5-yl)-urea, $K_i$=1,400 nM The title compound was prepared according to the general procedure in Example 1 using 4-bromophenyl isocyanate in place of 4-bromo-2-chlorophenyl isocyanate.

$^1$H NMR (400 MHz, CD$_3$OD): 7.39 (m, 2H), 7.30 (m, 4H), 7.22 (m, 1H), 7.12 (m, 2H), 5.31 (m, 1H), 4.38 (dd, J=12.0 Hz, 2.0 Hz, 1H), 3.99 (m, 1H), 3.81 (dd, J=12.0 Hz, 2.0 Hz, 1H), 1.62 (s, 3H), 1.56 (s, 3H).

Example 37

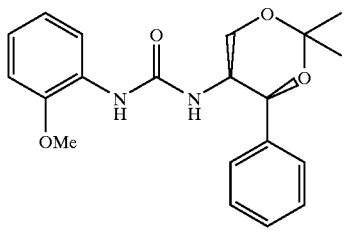

1-((4S,5S)-2,2-Dimethyl-4-phenyl-[1,3]dioxan-5-yl)-3-(2-methoxy-phenyl)-urea, $K_i$=6,000 nM The title compound was prepared according to the general procedure in Example 1 using 2-methoxyphenyl isocyanate in place of 4-bromo-2-chlorophenyl isocyanate.

$^1$H NMR (400 MHz, CD$_3$OD): 8.18 (br s, 1H), 7.74–7.67 (m, 1H), 7.42–7.36 (m, 2H), 7.32–7.25 (m, 2H), 7.23–7.12 (m, 2H), 6.90–6.84 (m, 2H), 6.80–6.73 (m, 1H), 5.29 (m, 1H), 4.36 (dd, J=12.0 Hz, J=2.0 Hz, 1H), 4.02–3.96 (m, 1H), 3.84–3.76 (m, 4H), 1.60 (s, 3H), 1.56 (s, 3H).

Example 38

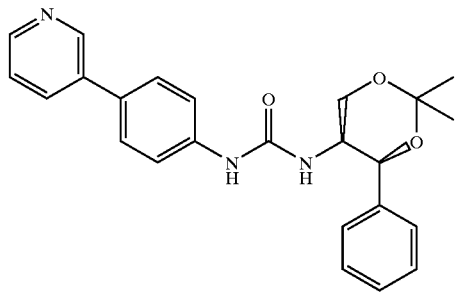

1-((4S,5S)-2,2-Dimethyl-4-phenyl-[1,3]dioxan-5-yl)-3-(4-pyridin-3-yl-phenyl)-urea, $K_i$=320 nM To a stirred solution of 10 mg (0.0088 mmol) of tetrakis(triphenylphosphine)palladium(0) in ethylene glycol dimethyl ether (2.0 mL) was added 100 mg (0.22 mmol) of the product from Example 7. After stirring for 15 min, 27 mg (0.22 mmol) of pyridine-3-boronic acid dissolved in ethanol (0.20 mL) was added followed by 0.22 mL (0.44 mmol) of a 2 M sodium carbonate aqueous solution. The reaction mixture was heated to 80° C. for 12 h and then cooled to room temperature. The mixture was taken up in 10 mL of dichloromethane and washed with water. The organic layers were dried over magnesium sulfate, filtered and concentrated in vacuo. The product was purified by chromatography (hexanes/ethyl acetate) to yield 40 mg (45%) of the title compound.

$^1$H NMR (400 MHz, CDCl$_3$): 8.72 (s, 1H), 8.43 (s, 1H), 8.01 (d, 7.81 Hz, 1H), 7.55–7.45 (m, 3H), 7.39 (m, 2H), 7.34–7.28 (m, 4H), 7.21 (m, 1H), 5.32 (s, 1H), 4.37 (d, 12.33 Hz, 1H), 3.99 (s, 1H), 3.81 (d, 11.78 Hz, 1H), 1.61 (s, 3H), 1.55 (s, 3H).

Example 39

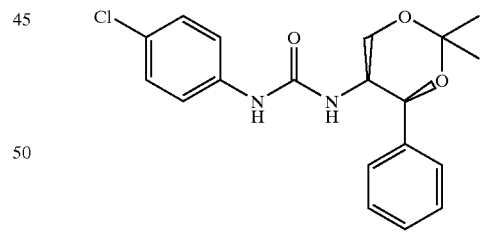

1-(4-Chloro-phenyl)-3-((4S,5S)-2,2-dimethyl-4-phenyl-[1,3]dioxan-5-yl)-urea, $K_i$=300 nM The title compound was prepared according to the general procedure in Example 1 using 4-chlorophenyl isocyanate in place of 4-bromo-2-chlorophenyl isocyanate.

$^1$H NMR (400 MHz, CD$_3$OD): 7.29–7.26 (m, 2H), 7.21–7.17 (m, 2H), 7.12–7.10 (m, 1H), 7.09–7.05 (m, 4H), 5.30 (s, 1H), 4.36 (dd, 11.8 Hz, 1.8 Hz, 1H), 3.96 (m, 1H), 3.79 (dd, 11.8 Hz, 1.8 Hz), 1.60 (s, 3H), 1.54 (s, 3H).

Example 40

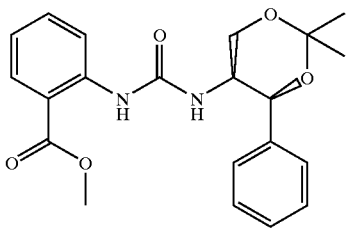

2-[3-((4S,5S)-2,2-Dimethyl-4-phenyl-[1,3]dioxan-5-yl)-ureido]-benzoic acid methyl ester, $K_i=1200$ nM The title compound was prepared according to the general procedure in Example 1 using methyl-2-isocyanatobenzoate in place of 4-bromo-2-chlorophenyl isocyanate.

$^1$H NMR (400 MHz, CD$_3$OD): 7.78 (dd, 8.0 Hz, 1.5 Hz, 1H), 7.66 (d, 1H), 7.32–7.25 (m, 3H), 7.17 (t, 7.3 Hz, 2H), 7.09 (m, 1H), 6.85 (t, 7.0 Hz, 1H), 5.21 (s, 1H), 4.31 (dd, 11.9 Hz, 2.0 Hz, 1H), 3.91 (s, 1H), 3.78 (s, 3H), 3.72 (dd, 11.9 Hz, 1.7 Hz, 1H), 1.50 (d, 14.3 Hz, 6H).

Example 41

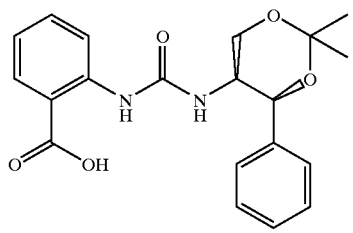

2-[3-((4S,5S)-2,2-Dimethyl-4-phenyl-[1,3]dioxan-5-yl)-ureido]-benzoic acid, $K_i=710$ nM The title compound was prepared upon treatment of the product of Example 40 with lithium hydroxide in aqueous THF.

$^1$H NMR (400 MHz, CD$_3$OD): 8.12–7.83 (m, 2H), 7.57–7.32 (m, 6H), 6.93 (m, 1H), 5.29 (s, 1H), 4.38 (m, 1H), 4.04 (s, 1H), 3.82 (d, 1.8 Hz, 1H), 1.24 (d, 2.0 Hz, 6H).

Example 42

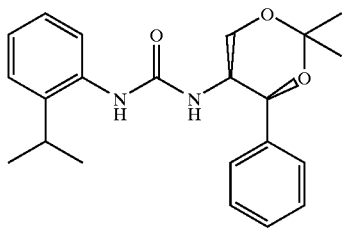

1-((4S,5S)-2,2-Dimethyl-4-phenyl-[1,3]dioxan-5-yl)-3-(2-isopropyl-phenyl)-urea, $K_i=2900$ nM The title compound was prepared according to the general procedure in Example 1 using 2-isopropylphenyl isocyanate in place of 4-bromo-2-chlorophenyl isocyanate.

$^1$H NMR (400 MHz, CD$_3$OD): 7.27–7.25 (m, 2H), 7.22–7.18 (m, 2H), 7.13–7.10 (m, 2H), 6.98 (m, 3H), 5.19 (s, 1H), 4.28 (dd, 11.8 Hz, 1.8 Hz, 1H), 3.93–3.90 (m, 1H), 3.70 (dd, 11.8 Hz, 1.9 Hz, 1H), 2.81 (m, 1H), 1.50 (s, 3H), 1.42 (s, 3H), 0.99 (t, 6.6 Hz, 6H).

Example 43

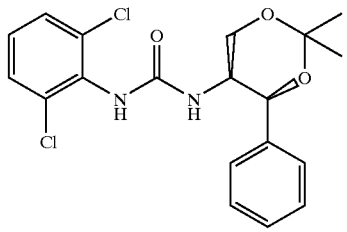

1-(2,6-Dichloro-phenyl)-3-((4S,5S)-2,2-dimethyl-4-phenyl-[1,3]dioxan-5-yl)-urea, $K_i=5000$ nM The title compound was prepared according to the general procedure in Example 1 using 2,6-dichlorophenyl isocyanate in place of 4-bromo-2-chlorophenyl isocyanate.

$^1$H NMR (400 MHz, CD$_3$OD): 7.28 (d, 7.5 Hz, 2H), 7.23–7.18 (m, 4H), 7.12 (m, 1H), 7.05 (t, 8.1 Hz, 1H), 5.19 (s, 1H), 4.29 (dd, 11.7 Hz, 1.8 Hz, 1H), 3.91 (m, 1H), 3.71 (dd, 11.8 Hz, 1.8 Hz, 1H), 1.52 (s, 3H), 1.46 (s, 3H).

Example 44

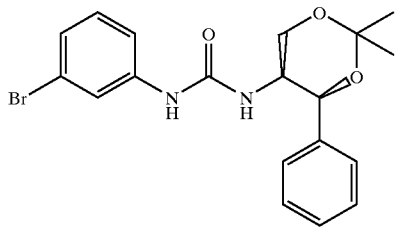

1-(3-Bromo-phenyl)-3-((4S,5S)-2,2-dimethyl-4-phenyl-[1,3]dioxan-5-yl)-urea, $K_i=3800$ nM The title compound was prepared according to the general procedure in Example 1 using 3-bromo-phenyl isocyanate in place of 4-bromo-2-chlorophenyl isocyanate.

$^1$H NMR (400 MHz, CD$_3$OD): 7.58 (s, 1H), 7.44 (d, 7.6 Hz, 2H), 7.36 (t, 8.0 Hz, 2H), 7.27 (m, 1H), 7.12–7.08 (m, 3H), 5.38 (s, 1H), 4.44 (dd, 11.8 Hz, 1.8 Hz, 1H), 4.04 (s, 1H), 3.87 (dd, 11.8 Hz, 1.8 Hz, 1H), 1.68 (s, 3H), 1.62 (s, 3H).

Example 45

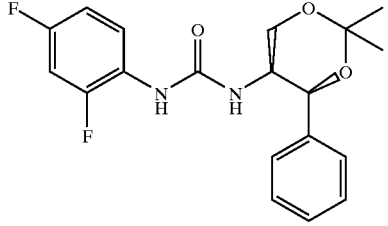

1-(2,4-Difluoro-phenyl)-3-((4S,5S)-2,2-dimethyl-4-phenyl-[1,3]dioxan-5-yl)-urea, $K_i=6,000$ nM The title compound was prepared according to the general procedure in Example 1 using 2,4-difluorophenyl isocyanate in place of 4-bromo-2-chlorophenyl isocyanate.

$^1$H NMR (400 MHz, CD$_3$OD): 7.71–7.65 (m, 1H), 7.40–7.38 (m, 2H), 7.31–7.27 (m, 2H), 7.23–7.19 (m, 1H), 6.93–6.87 (m, 1H), 6.81–6.75 (m, 1H), 5.30 (d, J=2.0 Hz, 1H), 4.38 (dd, J=12.0 Hz, J=2.0 Hz, 1H), 3.97 (d, J=2.0 Hz, 1H), 3.80 (dd, J=12.0 Hz, J=2.0 Hz, 1H), 1.61 (s, 3H), 1.56 (s, 3H).

Example 46

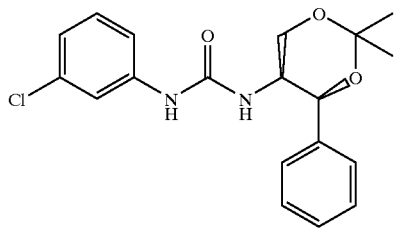

1-(3-Chloro-phenyl)-3-((4S,5S)-2,2-dimethyl-4-phenyl-[1,3]dioxan-5-yl)-urea, K$_i$=2000 nM The title compound was prepared according to the general procedure in Example 1 using 3-chlorophenyl isocyanate in place of 4-bromo-2-chlorophenyl isocyanate.

$^1$H NMR (400 MHz, CD$_3$OD): 7.39–7.35 (m, 3H), 7.29 (t, 7.5 Hz, 2H), 7.21 (m, 1H), 7.12 (t, 8.1 Hz, 1H), 7.00 (m, 1H), 6.89 (m, 1H), 5.31 (s, 1H), 4.37 (dd, 11.8 Hz, 1.8 Hz, 1H), 3.98 (s, 1H), 3.80 (dd, 11.8 Hz, 1.8 Hz, 1H), 1.61 (s, 3H), 1.55 (s, 3H).

Example 47

Orexin Binding Assays

Determination of receptor binding characteristics for compounds described in the invention was accomplished using adherent, cultured recombinant cells and radioiodinated orexin A. Recombinant clones were generated in HEK-293 and CHO-K1 cells, with the latter preferred because they adhere more tightly to the cell culture plate.

Radioiodinated orexin A was prepared by reacting 10 μg orexin A with 1 mCi Na$^{125}$I and 10 μg chloramine-T in 70 μL of 70 mM potassium phosphate buffer (pH 7.4) for 30 sec at room temperature. The reaction was quenched with 100 μL of 10% w/v bovine serum albumin, then the products were pre-purified using Waters Maxi-Clean C18 cartridges (Alltech, San Jose, Calif.). The mobile phase for the reverse phase separations (pre-purification and gradient HPLC) was 0.1% TFA, and the eluent was 0.1% TFA in acetonitrile. After removing the acetonitrile from the Maxi-Clean cartridge eluent by lyophilization, the labeled compound was further purified by gradient HPLC using a Vydac (Hesperia, Calif.) analytical C18 HPLC column. A gradient of 2% acetonitrile/min was used and fractions were collected every 0.75 min at a flow rate of 1.5 mL/min. Baseline separation was achieved between the iodinated product and reagents. The specific activity was estimated at 2200 Ci/mmol.

Radioligand binding assays were performed in opaque, white 96-well tissue culture plates pretreated with poly-D-lysine (Bio-Coat plates, Becton Dickinson, Franklin Lakes, N.J.). Cells expressing the orexin receptor were seeded at 30,000 cells/well in 100 μL/well Ham's F12 with 10% heat inactivated fetal bovine serum, penicillin/streptomycin and 800 mg/L G418. Four days later the cells had grown to confluence and were ready for the binding reaction. In preparation for the binding assay, the cell culture medium was aspirated away, and the cells were gently washed with 100 μL-well binding buffer (Dulbecco's phosphate buffered saline containing 0.1% w/v bovine serum albumin). The remaining components of the radioligand binding reaction (100,000 cpm $^{125}$I-orexin A and test compounds or controls in binding buffer) were then added to the cells and incubated for 90 to 120 min at room temperature. The assay was terminated by aspirating the liquid from the wells, washing the wells with iced binding buffer, aspirating the wells dry, adding 50 μL/well scintillation cocktail (MicroScint 40, Packard Biosciences, Meriden Conn.), and counting the plate(s) in a Packard TopCount scintillation counter. The cells expressing the orexin receptor remained attached to the tissue culture plate until the scintillation fluid was added. Data were analyzed using GraphPad Prizm software to calculate K$_i$ values.

Cell Culture

PFSK-1 cells were obtained from the American Type Culture Collection (CRL-2060; Manassas, Va.) and cultured as described by Fults et al. (*J. Neuropathology Exp. Neurology*, 1992, 51 (3):272–280). Cells were grown on 10 or 15 cm tissue culture dishes (Corning Inc., Corning, N.Y.) in RPMI medium 1640 containing 25 mM Hepes and L-glutamine (Gibco/InVitrogen, Carlsbad, Calif.) supplemented with 10% fetal bovine serum (HyClone, Logan, Utah), 50 u/mL penicillin G, and 50 u/mL streptomycin sulphate. Cells grown on 10 dishes were grown in 10 mL complete medium, and cells grown on 15 cm dishes were grown in 30 mL complete medium. Cells were passed every 3 to 5 days at a 1:5 dilution by aspirating away the medium, adding 2 mL/dish Gibco/Invitrogen Trypsin-EDTA solution, aspirating away the solution, incubating at room temperature 5 min, and dispersing the cells into fresh plates using fresh complete medium. Cells were then maintained in incubators set to maintain 37° C. and 5% CO$_2$.

Intracellular Calcium Ion Measurement

Agonist binding of orexin receptors elevates the intracellular free calcium ion concentration through the activation of a Gq protein and the opening of voltage-activated plasmalemmal calcium channels (see: A. N. Van Den Pol et al. *J. Neurosci.*, 1998, 18(19):7962–7971). This effect was monitored using the fluorescent Ca$^{++}$ indicator Fluo-3 AM (TefLabs, Austin, Tex.) and the Molecular Devices (Sunnyvale, Calif.) FLIPR instrument.

PFSK-1 cells were removed from confluent tissue culture dishes with trypsin-EDTA as described above and plated in 96-well Packard Viewplates (Meriden, Conn.) at 50,000 cells/well in 100 μL/well complete medium. The next day the cells, which adhered to the Viewplates and grew to confluency, were loaded with the fluorescent dye. For each Viewplate 20 μL of 2.3 μM Fluo-3 AM was mixed with 20 μL 20% F-127 detergent (Molecular Probes, Eugene, Oreg.) and that mixture was mixed into 10 mL Gibco/Invitrogen D-MEM:F12. After removing the complete growth medium from the Viewplate, 100 μL of the Fluo-3 AM solution was added to each well. The plate was incubated at room temperature for 60 min or at 37° C. for 30 min. Test compounds were added to the wells in an isotonic, pH-neutral vehicle, such as Dulbecco's phosphate-buffered saline, and changes in intracellular calcium concentrations were measured using the FLIPR instrument.

For screening purposes compounds were tested at a single dose (10 μM) to determine the % inhibition of intracellular Ca$^{++}$ signalling compared to a 100 nM orexin agonist stimulus. The compounds were delivered to the test wells, and the compounds and the cells were incubated to allow binding. Then the orexin agonist stimulus was added to the test wells. The control column for the antagonist screen included positive and negative controls to indicate the fluorescence of a full agonist response and the baseline.

Antagonism was analyzed by calculating $K_B$ and $pK_B$ values for compounds found to inhibit increases in intracellular $Ca^{++}$ concentrations of PFSK-1 cells. This was accomplished by determining the $EC_{50}$ of orexin B and comparing the $IC_{50}$ values determined from dilutions of antagonist compound(s), all on a single 96-well Viewplate of PFSK-1 cells loaded with Fluo-3 AM. In this case all of the wells except those used to determine the agonist's $EC_{50}$ were given the same concentration of the orexin agonist (100 nM). The $K_B$ is then determined after Y.-C. Cheng and W. H. Prusoff (*Biochem. Pharmacol.*, 1973, 22(23): 3099–3108) using the formula below:

$$K_B = IC_{50}/(1+(\{agonist\}/EC_{50}))$$

The table below shows $pK_B$ values for some of the most preferred compounds. $PK_B$ values for other compounds may be different. The range of $pK_B$ values of compounds within the invention that were tested to date was between <5 and 8.3. Based on the assay method, values below 5 were not measurable. Higher values, such as 7 or 8 or more, are generally preferred.

| Example | $pK_B$ |
|---------|--------|
| 1 | 7.6 |
| 4 | 8.3 |
| 5 | 7.6 |
| 12 | 8.2 |

F. Other Embodiments

The features and advantages of the invention are apparent to one of ordinary skill in the art. Based on this disclosure, including the summary, detailed description, background, examples, and claims, one of ordinary skill in the art will be able to make modifications and adaptations to various conditions and usages. These other embodiments are also within the scope of the invention.

What is claimed is:

1. A pharmaceutical composition comprising a pharmaceutically-acceptable carrier and a compound of formula (I):

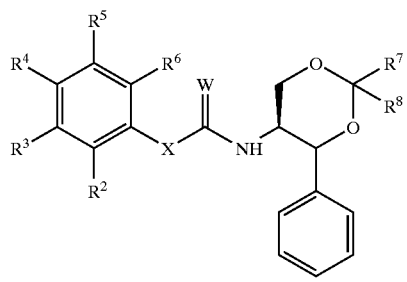

wherein:

$R^2$ is H, F, Cl, Br, I, cyano, nitro, $COR^a$, $COOR^a$, $C_{1-6}$ alkyl, $C_{1-6}$ alkoxy, $C_{1-6}$ alkylthio, $C_{1-6}$ haloalkyl, $C_{3-7}$ cycloalkyl, phenyl, $C_{2-9}$ heterocyclyl, (phenyl)-$C_{1-6}$ alkylene, ($C_{2-9}$ heterocyclyl)-$C_{1-6}$ alkylene, or ($C_{3-7}$ cycloalkyl)-$C_{1-6}$ alkylene; wherein $R^a$ is H, $C_{1-6}$ alkyl, $C_{3-7}$ cycloalkyl, or ($C_{3-7}$ cycloalkyl)-$C_{1-6}$ alkylene;

$R^3$ is H, F, Cl, Br, I, cyano, hydroxy, nitro, amino, $C_{1-6}$ alkyl, $C_{1-6}$ alkoxy, $C_{1-6}$ alkylthio, $C_{1-6}$ haloalkyl, $C_{3-7}$ cycloalkyl, phenyl, $C_{2-9}$ heterocyclyl, (phenyl)-$C_{1-6}$ alkylene, ($C_{2-9}$ heterocyclyl)-$C_{1-6}$ alkylene, or ($C_{3-7}$ cycloalkyl)-$C_{1-6}$ alkylene or $R^2$ and $R^3$ taken together with the phenyl ring to which they are attached form a naphthyl;

$R^4$ is H, F, Cl, Br, I, cyano, hydroxy, nitro, amino, $COR^b$, $COOR^b$, $C_{1-6}$ alkyl, $C_{1-6}$ alkoxy, $C_{1-6}$ alkylthio, $C_{1-6}$ haloalkyl, $C_{3-7}$ cycloalkyl, phenyl, $C_{2-9}$ heterocyclyl, (phenyl)-$C_{1-6}$ alkylene, ($C_{2-9}$ heterocyclyl)-$C_{1-6}$ alkylene, or ($C_{3-7}$ cycloalkyl)-$C_{1-6}$ alkylene; wherein $R^b$ is H, $C_{1-6}$ alkyl, $C_{3-7}$ cycloalkyl, or ($C_{3-7}$ cycloalkyl)-$C_{1-6}$ alkylene;

$R^5$ is H, F, Cl, Br, I, cyano, hydroxy, nitro, amino, $C_{1-6}$ alkyl, $C_{1-4}$ alkoxy, $C_{1-6}$ alkylthio, $C_{1-6}$ haloalkyl, or $C_{3-7}$ cycloalkyl;

$R^6$ is H, F, Cl, Br, I, cyano, hydroxy, nitro, amino, $C_{1-6}$ alkyl, $C_{1-6}$ alkoxy, $C_{1-6}$ alkylthio, $C_{1-6}$ haloalkyl, $C_{3-7}$ cycloalkyl, phenyl, $C_{2-9}$ heterocyclyl, (phenyl)-$C_{1-6}$ alkylene, ($C_{2-9}$ heterocyclyl)-$C_{1-6}$ alkylene, or ($C_{3-7}$ cycloalkyl)-$C_{1-6}$ alkylene;

X is NH, O, or $CH_2$;

W is S, O, or =N—CN;

each of $R^7$ and $R^8$ is independently selected from H, $C_{1-6}$ alkyl, $C_{3-7}$ cycloalkyl, ($C_{3-7}$ cycloalkyl)-$C_{1-6}$ alkylene, phenyl, and (phenyl)-$C_{1-6}$ alkylene, provided at least one of $R^7$ and $R^8$ is not H;

wherein each of the above hydrocarbyl or heterocarbyl moieties can be optionally substituted with between 1 and 3 substituents selected from F, Cl, Br, I, cyano, hydroxy, nitro, amino, $COR^c$, $COOR^c$, $C_{1-3}$ alkyl, $C_{1-3}$ alkoxy, $C_{1-3}$ alkylthio, $C_{1-3}$ haloalkyl, and $C_{3-6}$ cycloalkyl; wherein $R^c$ is H or $C_{1-6}$ alkyl;

provided when W is O, X is NH, and $R^7$ and $R^8$ are each methyl, and $R^3$, $R^4$, $R^5$, and $R^6$ are each H, then $R^2$ is not H, 2-chlorophenyl, or 3-quinolinyl;

and pharmaceutically acceptable salts, esters, amides, and hydrates thereof.

2. A composition of claim 1, wherein W is O.

3. A composition of claim 1, wherein $R^2$ and $R^4$ are not hydrogen.

4. A composition of claim 1, wherein X is $CH_2$.

5. A composition of claim 1, wherein X is NH.

6. A composition of claim 1, wherein each of $R^7$ and $R^8$ is independently selected from methyl, ethyl, and propyl.

7. A composition of claim 1, wherein at least two of $R^3$, $R^5$, and $R^6$ are H.

8. A composition of claim 1, wherein $R^2$ is H, Cl, Br, I, methyl, halomethyl, cyano, amino, $C_{2-9}$ heterocyclyl, phenyl, or phenyl substituted with hydroxy, thiol, nitro, cyano, or halo.

9. A composition of claim 8, wherein $R^2$ is Cl, Br, I, methyl, cyano, $C_{2-9}$ heteroaryl, phenyl, or phenyl substituted with hydroxy, thiol, or halo.

10. A composition of claim 1, wherein $R^3$ is H or methyl.

11. A composition of claim 10, wherein $R^3$ is H.

12. A composition of claim 1, wherein $R^4$ is H, Cl, Br, I, methyl, halomethyl, cyano, amino, $C_{2-9}$ heterocyclyl, phenyl, or phenyl substituted with hydroxy, thiol, nitro, cyano, or halo.

13. A composition of claim 12, wherein $R^4$ is H, Cl, Br, I, or methyl.

14. A composition of claim 1, wherein $R^5$ is H, Cl, Br, I, methyl, halomethyl, methoxy, thiomethyl, ethyl, ethoxy, or thioethyl.

15. A composition of claim 14, wherein $R^5$ is H, methyl, or Cl.

16. A composition of claim 1, wherein the stereochemistry of the two dioxane chiral centers is (S,S).

17. A composition of claim 1, wherein said compound of formula (I) is selected from:

1-(2-Bromo-phenyl)-3-(2,2-dimethyl-4-phenyl-[1,3]dioxan-5-yl)-urea;
1-Biphenyl-2-yl-3-(2,2-dimethyl-4-phenyl-[1,3]dioxan-5-yl)-urea; and
1-(2,3-Dichloro-phenyl)-3-(2,2-dimethyl-4-phenyl-[1,3]dioxan-5-yl)-urea.

18. A composition of claim 1, wherein said compound of formula (I) is selected from:

1-(4-Bromo-2-chloro-phenyl)-3-((4S,5S)-2,2-dimethyl-4-phenyl-[1,3]dioxan-5-yl)-urea;
1-(2,4-Dibromo-phenyl)-3-((4S,5S)-2,2-dimethyl-4-phenyl-[1,3]dioxan-5-yl)-urea;
1-(2,4-Dichloro-phenyl)-3-((4S,5S)-2,2-dimethyl-4-phenyl-[1,3]dioxan-5-yl)-urea;
1-(2-Chloro-5-methyl-phenyl)-3-((4S,5S)-2,2-dimethyl-4-phenyl-[1,3]dioxan-5-yl)-urea;
1-((4S,5S)-2,2-Dimethyl-4-phenyl-[1,3]dioxan-5-yl)-3-(2-thiophen-2-yl-phenyl)-urea;
1-((4S,5S)-2,2-Dimethyl-4-phenyl-[1,3]dioxan-5-yl)-3-(2-iodo-phenyl)-urea;
1-((4S,5S)-2,2-Dimethyl-4-phenyl-[1,3]dioxan-5-yl)-3-(4-iodo-phenyl)-urea;
1-(4-Bromo-2-methyl-phenyl)-3-((4S,5S)-2,2-dimethyl-4-phenyl-[1,3]dioxan-5-yl)-urea;
1-(2-Bromo-4-methyl-phenyl)-3-((4S,5S)-2,2-dimethyl-4-phenyl-[1,3]dioxan-5-yl)-urea;
1-(2-Cyano-phenyl)-3-((4S,5S)-2,2-dimethyl-4-phenyl-[1,3]dioxan-5-yl)-urea;
1-(3'-Chloro-biphenyl-2-yl)-3-((4S,5S)-2,2-dimethyl-4-phenyl-[1,3]dioxan-5-yl)-urea;
1-(2,5-Dimethyl-phenyl)-3-((4S,5S)-2,2-dimethyl-4-phenyl-[1,3]dioxan-5-yl)-urea; and
1-Biphenyl-2-yl-3-((4S,5S)-2,2-dimethyl-4-phenyl-[1,3]dioxan-5-yl)-urea.

19. A composition of claim 1, wherein said compound of formula (I) is selected from:

1-((4S,5S)-2,2-Dimethyl-4-phenyl-[1,3]dioxan-5-yl)-3-(2-trifluoromethyl-phenyl)-urea;
1-(4-Bromo-3-methyl-phenyl)-3-((4S,5S)-2,2-dimethyl-4-phenyl-[1,3]dioxan-5-yl)-urea;
1-(2-Bromo-phenyl)-3-((4S,5S)-2,2-dimethyl-4-phenyl-[1,3]dioxan-5-yl)-urea;
1-(2,5-Dichloro-phenyl)-3-((4S,5S)-2,2-dimethyl-4-phenyl-[1,3]dioxan-5-yl)-urea;
1-(2-Chloro-5-trifluoromethyl-phenyl)-3-((4S,5S)-2,2-dimethyl-4-phenyl-[1,3]dioxan-5-yl)-urea;
1-(2-Bromo-phenyl)-3-((4R,5S)-2,2-dimethyl-4-phenyl-[1,3]dioxan-5-yl)-urea; and
1-((4S,5S)-2,2-Dimethyl-4-phenyl-[1,3]dioxan-5-yl)-3-(2-thiophen-3-yl-phenyl)-urea.

20. A composition of claim 1, wherein said compound of formula (I) is selected from:

1-(2,4-Dimethyl-phenyl)-3-((4S,5S)-2,2-dimethyl-4-phenyl-[1,3]dioxan-5-yl)-urea;
1-(2-Chloro-phenyl)-3-((4S,5S)-2,2-dimethyl-4-phenyl-[1,3]dioxan-5-yl)-urea;
1-((4S,5S)-2,2-Dimethyl-4-phenyl-[1,3]dioxan-5-yl)-3-(2-fluoro-phenyl)-urea;
1-((4S,5S)-2,2-Dimethyl-4-phenyl-[1,3]dioxan-5-yl)-3-o-tolyl-urea;
1-((4S,5S)-2,2-Dimethyl-4-phenyl-[1,3]dioxan-5-yl)-3-(2-nitro-phenyl)-urea;
2-(2-Bromo-phenyl)-N-((4S,5S)-2,2-dimethyl-4-phenyl-[1,3]dioxan-5-yl)-acetamide;
((4S,5S)-2,2-Dimethyl-4-phenyl-[1,3]dioxan-5-yl)-carbamic acid 2-chloro-phenyl ester;
1-(4-Bromo-phenyl)-3-((4S,5S)-2,2-dimethyl-4-phenyl-[1,3]dioxan-5-yl)-urea;
1-((4S,5S)-2,2-Dimethyl-4-phenyl-[1,3]dioxan-5-yl)-3-(2-methoxy-phenyl)-urea;
1-(4-Chloro-phenyl)-3-((4S,5S)-2,2-dimethyl-4-phenyl-[1,3]dioxan-5-yl)-urea;
2-[3-((4S,5S)-2,2-Dimethyl-4-phenyl-[1,3]dioxan-5-yl)-ureido]-benzoic acid;
2-[3-((4S,5S)-2,2-Dimethyl-4-phenyl-[1,3]dioxan-5-yl)-ureido]-benzoic acid methyl ester;
1-((4S,5S)-2,2-Dimethyl-4-phenyl-[1,3]dioxan-5-yl)-3-(2-isopropyl-phenyl)-urea;
1-(2,6-Dichloro-phenyl)-3-((4S,5S)-2,2-dimethyl-4-phenyl-[1,3]dioxan-5-yl)-urea;
1-(3-Bromo-phenyl)-3-((4S,5S)-2,2-dimethyl-4-phenyl-[1,3]dioxan-5-yl)-urea;
1-(2,4-Difluoro-phenyl)-3-((4S,5S)-2,2-dimethyl-4-phenyl-[1,3]dioxan-5-yl)-urea; and
1-(3-Chloro-phenyl)-3-((4S,5S)-2,2-dimethyl-4-phenyl-[1,3]dioxan-5-yl)-urea.

21. A compound of formula (Ia):

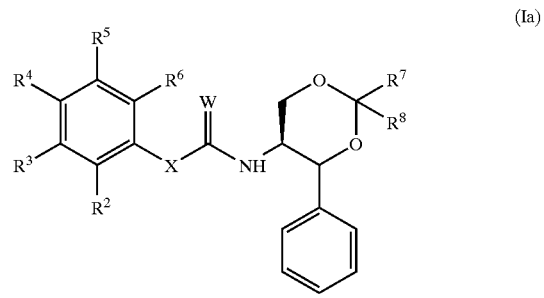

(Ia)

wherein:

R is H, F, Cl, Br, I, cyano, nitro, $COR^a$, $COOR^a$, $C_{1-6}$ alkyl, $C_{1-6}$ alkoxy, $C_{1-6}$ alkylthio, $C_{1-6}$ haloalkyl, $C_{3-7}$ cycloalkyl, phenyl, $C_{2-9}$ heterocyclyl, (phenyl)-$C_{1-6}$ alkylene, ($C_{2-9}$ heterocyclyl)-$C_{1-6}$ alkylene, or ($C_{3-7}$ cycloalkyl)-$C_{1-6}$ alkylene; wherein $R^a$ is H, $C_{1-6}$ alkyl, $C_{3-7}$ cycloalkyl, or ($C_{3-7}$ cycloalkyl)-$C_{1-6}$ alkylene;

$R^3$ is H, F, Cl, Br, I, cyano, hydroxy, nitro, amino, $C_{1-6}$ alkyl, $C_{1-6}$ alkoxy, $C_{1-6}$ alkylthio, $C_{1-6}$ haloalkyl, $C_{3-7}$ cycloalkyl, phenyl, $C_{2-9}$ heterocyclyl, (phenyl)-$C_{1-6}$ alkylene, ($C_{2-9}$ heterocyclyl)-$C_{1-6}$ alkylene, or ($C_{3-7}$ cycloalkyl)-$C_{1-6}$ alkylene or $R^2$ and $R^3$ taken together with the phenyl ring to which they are attached form a naphthyl;

$R^4$ is H, F, Cl, Br, 1, cyano, hydroxy, nitro, amino, $COR^b$, $COOR^b$, $C_{1-6}$ alkyl, $C_{1-6}$ alkoxy, $C_{1-6}$ alkylthio, $C_{1-6}$ haloalkyl, $C_{3-7}$ cycloalkyl, phenyl, $C_{2-9}$ heterocyclyl, (phenyl)-$C_{1-6}$ alkylene, ($C_{2-9}$ heterocyclyl)-$C_{1-6}$ alkylene, or ($C_{3-7}$ cycloalkyl)-$C_{1-6}$ alkylene; wherein $R^b$ is H, $C_{1-6}$ alkyl, $C_{3-7}$ cycloalkyl, or ($C_{3-7}$ cycloalkyl)-$C_{1-6}$ alkylene;

$R^5$ is H, F, Cl, Br, 1, cyano, hydroxy, nitro, amino, $C_{1-6}$ alkyl, $C_{1-6}$ alkoxy, $C_{1-6}$ alkylthio, $C_{1-6}$ haloalkyl, or $C_{3-7}$ cycloalkyl;

R⁶ is H, F, Cl, Br, I, cyano, hydroxy, nitro, amino, $C_{1-6}$ alkyl, $C_{1-6}$ alkoxy, $C_{1-6}$ alkylthio, $C_{1-6}$ haloalkyl, $C_{3-7}$ cycloalkyl, phenyl, $C_{2-9}$ heterocyclyl, (phenyl)-$C_{1-6}$ alkylene, ($C_{2-9}$ heterocyclyl)-$C_{1-6}$ alkylene, or ($C_{3-7}$ cycloalkyl)-$C_{1-6}$ alkylene;

X is NH, O, or $CH_2$;

W is S, O, or =N—CN;

each of R⁷ and R⁸ is independently selected from H, $C_{1-6}$ alkyl, $C_{3-7}$ cycloalkyl, ($C_{3-7}$ cycloalkyl)-$C_{1-6}$ alkylene, phenyl, and (phenyl)-$C_{1-6}$ alkylene, provided at least one of R⁷ and R⁸ is not H;

wherein each of the above hydrocarbyl or heterocarbyl moieties can be optionally substituted with between 1 and 3 substituents selected from F, Cl, Br, I, cyano, hydroxy, nitro, amino, $COR^c$, $COOR^c$, $C_{1-3}$ alkyl, $C_{1-3}$ alkoxy, $C_{1-3}$ alkylthio, $C_{1-3}$ haloalkyl, and $C_{3-6}$ cycloalkyl; wherein $R^c$ is H or $C_{1-6}$ alkyl;

provided when W is O, X is NH, and R⁷ and R⁸ are each methyl, and R³, R⁴, R⁵, and R⁶ are each H, then R² is not H, Br, phenyl, 2-chlorophenyl, or 3-quinolinyl;

provided when W is O, X is NH, and R⁷ and R⁸ are each methyl, and R⁴, R⁵, and R⁶ are each H, then R³ is not Cl nor is R³ taken together with R²; and provided when W is O, X is NH, and R⁷ and R⁸ are each methyl, and R², R⁵, and R⁶ are each H, then R⁴ is not Cl;

and pharmaceutically acceptable salts, esters, amides, and hydrates thereof.

22. A compound of claim 21, wherein W is O.

23. A compound of claim 21, wherein R² and R⁴ are not hydrogen.

24. A compound of claim 21, wherein X is $CH_2$.

25. A compound of claim 21, wherein X is NH.

26. A compound of claim 21, wherein each of R⁷ and R⁸ is independently selected from methyl, ethyl, and propyl.

27. A compound of claim 21, wherein at least two of R³, R⁵, and R⁶ are H.

28. A compound of claim 21, wherein R² is H, Cl, Br, I, methyl, halomethyl, cyano, amino, $C_{2-9}$ heterocyclyl, phenyl, or phenyl substituted with hydroxy, thiol, nitro, cyano, or halo.

29. A compound of claim 28, wherein R² is Cl, Br, I, methyl, cyano, $C_{2-9}$ heteroaryl, phenyl, or phenyl substituted with hydroxy, thiol, or halo.

30. A compound of claim 21, wherein R³ is H or methyl.

31. A compound of claim 30, wherein R³ is H.

32. A compound of claim 21, wherein R⁴ is H, Cl, Br, I, methyl, halomethyl, cyano, amino, $C_{2-9}$ heterocyclyl, phenyl, or phenyl substituted with hydroxy, thiol, nitro, cyano, or halo.

33. A compound of claim 32, wherein R⁴ is H, Cl, Br, I, or methyl.

34. A compound of claim 21, wherein R⁵ is H, Cl, Br, I, methyl, halomethyl, methoxy, thiomethyl, ethyl, ethoxy, or thioethyl.

35. A compound of claim 34, wherein R⁵ is H, methyl, or Cl.

36. A compound of claim 21, wherein the stereochemistry of the two chiral centers is (S,S).

37. A compound of claim 21, wherein said compound of formula (Ia) is selected from:

1-(4-Bromo-2-chloro-phenyl)-3-((4S,5S)-2,2-dimethyl-4-phenyl-[1,3]dioxan-5-yl)-urea;

1-(2,4-Dibromo-phenyl)-3-((4S,5S)-2,2-dimethyl-4-phenyl-[1,3]dioxan-5-yl)-urea;

1-(2,4-Dichloro-phenyl)-3-((4S,5S)-2,2-dimethyl-4-phenyl-[1,3]dioxan-5-yl)-urea;

1-(2-Chloro-5-methyl-phenyl)-3-((4S,5S)-2,2-dimethyl-4-phenyl-[1,3]dioxan-5-yl)-urea;

1-((4S,5S)-2,2-Dimethyl-4-phenyl-[1,3]dioxan-5-yl)-3-(2-thiophen-2-yl-phenyl)-urea;

1-((4S,5S)-2,2-Dimethyl-4-phenyl-[1,3]dioxan-5-yl)-3-(2-iodo-phenyl)-urea;

1-((4S,5S)-2,2-Dimethyl-4-phenyl-[1,3]dioxan-5-yl)-3-(4-iodo-phenyl)-urea;

1-(4-Bromo-2-methyl-phenyl)-3-((4S,5S)-2,2-dimethyl-4-phenyl-[1,3]dioxan-5-yl)-urea;

1-(2-Bromo-4-methyl-phenyl)-3-((4S,5S)-2,2-dimethyl-4-phenyl-[1,3]dioxan-5-yl)-urea;

1-(2-Cyano-phenyl)-3-((4S,5S)-2,2-dimethyl-4-phenyl-[1,3]dioxan-5-yl)-urea;

1-(3'-Chloro-biphenyl-2-yl)-3-((4S,5S)-2,2-dimethyl-4-phenyl-[1,3]dioxan-5-yl)-urea; and 1-(2,5-Dimethyl-phenyl)-3-((4S,5S)-2,2-dimethyl-4-phenyl-[1,3]dioxan-5-yl)-urea.

38. A compound of claim 21, wherein said compound of formula (Ia) is selected from:

1-((4S,5S)-2,2-Dimethyl-4-phenyl-[1,3]dioxan-5-yl)-3-(2-trifluoromethyl-phenyl)-urea;

1-(4-Bromo-3-methyl-phenyl)-3-((4S,5S)-2,2-dimethyl-4-phenyl-[1,3]dioxan-5-yl)-urea;

1-(2,5-Dichloro-phenyl)-3-((4S,5S)-2,2-dimethyl-4-phenyl-[1,3]dioxan-5-yl)-urea;

1-(2-Chloro-5-trifluoromethyl-phenyl)-3-((4S,5S)-2,2-dimethyl-4-phenyl-[1,3]dioxan-5-yl)-urea; and 1-((4S,5S)-2,2-Dimethyl-4-phenyl-[1,3]dioxan-5-yl)-3-(2-thiophen-3-yl-phenyl)-urea.

39. A compound of claim 21, wherein said compound of formula (Ia) is selected from:

1-(2,4-Dimethyl-phenyl)-3-((4S,5S)-2,2-dimethyl-4-phenyl-[1,3]dioxan-5-yl)-urea;

1-(2-Chloro-phenyl)-3-((4S,5S)-2,2-dimethyl-4-phenyl-[1,3]dioxan-5-yl)-urea;

1-((4S,5S)-2,2-Dimethyl-4-phenyl-[1,3]dioxan-5-yl)-3-(2-fluoro-phenyl)-urea;

1-((4S,5S)-2,2-Dimethyl-4-phenyl-[1,3]dioxan-5-yl)-3-o-tolyl-urea;

1-((4S,5S)-2,2-Dimethyl-4-phenyl-[1,3]dioxan-5-yl)-3-(2-nitro-phenyl)-urea;

2-(2-Bromo-phenyl)-N-((4S,5S)-2,2-dimethyl-4-phenyl-[1,3]dioxan-5-yl)-acetamide;

((4S,5S)-2,2-Dimethyl-4-phenyl-[1,3]dioxan-5-yl)-carbarmic acid 2-chloro-phenyl ester;

1-(4-Bromo-phenyl)-3-((4S,5S)-2,2-dimethyl-4-phenyl-[1,3]dioxan-5-yl)-urea;

1-((4S,5S)-2,2-Dimethyl-4-phenyl-[1,3]dioxan-5-yl)-3-(2-methoxy-phenyl)-urea;

2-[3-((4S,5S)-2,2-Dimethyl-4-phenyl-[1,3]dioxan-5-yl)-ureido]-benzoic acid;

2-[3-((4S,5S)-2,2-Dimethyl-4-phenyl-[1,3]dioxan-5-yl)-ureido]-benzoic acid methyl ester;

1-((4S,5S)-2,2-Dimethyl-4-phenyl-[1,3]dioxan-5-yl)-3-(2-isopropyl-phenyl)-urea;

1-(2,6-Dichloro-phenyl)-3-((4S,5S)-2,2-dimethyl-4-phenyl-[1,3]dioxan-5-yl)-urea;

1-(3-Bromo-phenyl)-3-((4S,5S)-2,2-dimethyl-4-phenyl-[1,3]dioxan-5-yl)-urea; and 1-(2,4-Difluoro-phenyl)-3-((4S,5S)-2,2-dimethyl-4-phenyl-[1,3]dioxan-5-yl)-urea.

40. A method for treating obesity, said method comprising administering to a subject a pharmaceutically-effective amount of a pharmaceutical composition of claim 1.

41. A method for treating a sleep/wake disorder, said method comprising administering to a subject a pharmaceutically-effective amount of a pharmaceutical composition of claim 1.

42. A method of claim 41, wherein said sleep/wake disorder is selected from insomnia, narcolepsy, jet lag, and sleep apnea.

43. A compound of claim 21, wherein said compound is selective for orexin-2 receptor over orexin-1 receptor by a factor of at least 10.

44. A compound of claim 43, wherein said factor is at least 100.

* * * * *

UNITED STATES PATENT AND TRADEMARK OFFICE
CERTIFICATE OF CORRECTION

PATENT NO. : 6,951,882 B2
DATED : October 4, 2005
INVENTOR(S) : Nicholas I. Carruthers et al.

It is certified that error appears in the above-identified patent and that said Letters Patent is hereby corrected as shown below:

Column 48,
Line 45, change "R" to read -- $R^2$ --.
Lines 58 and 65 change "1" to read -- I --.

Signed and Sealed this

Seventeenth Day of January, 2006

JON W. DUDAS
*Director of the United States Patent and Trademark Office*